Figure 1:
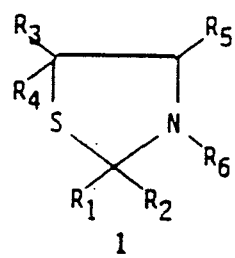
Figure 2:
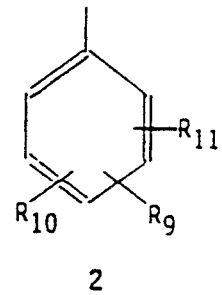
Figure 3:
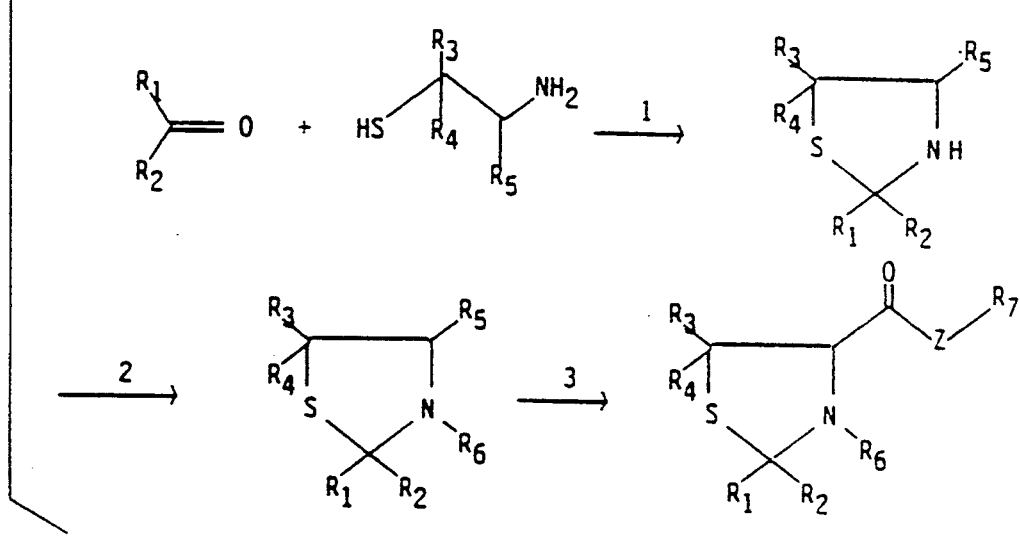
Figure 4:
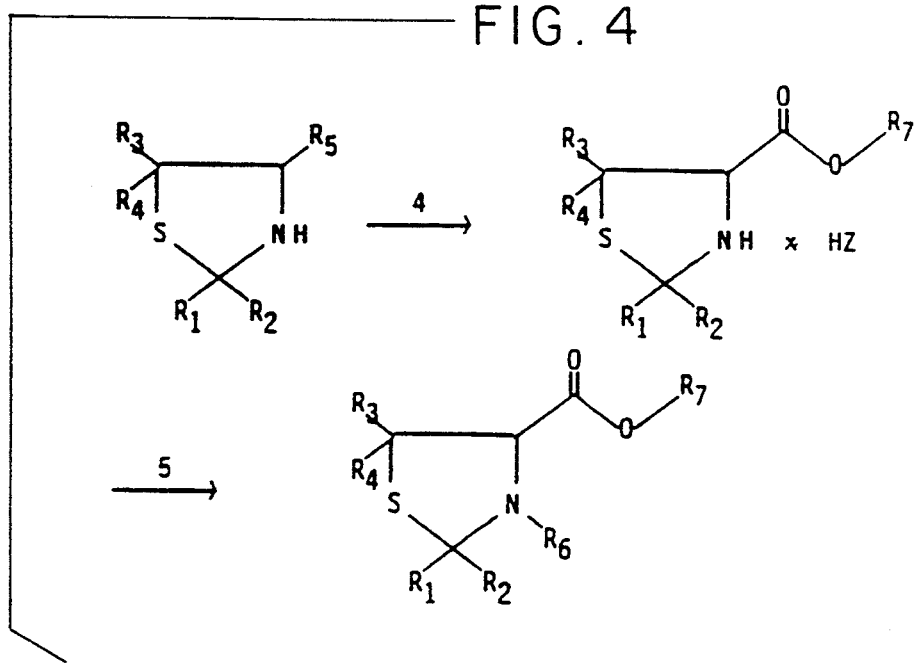
Figure 5:
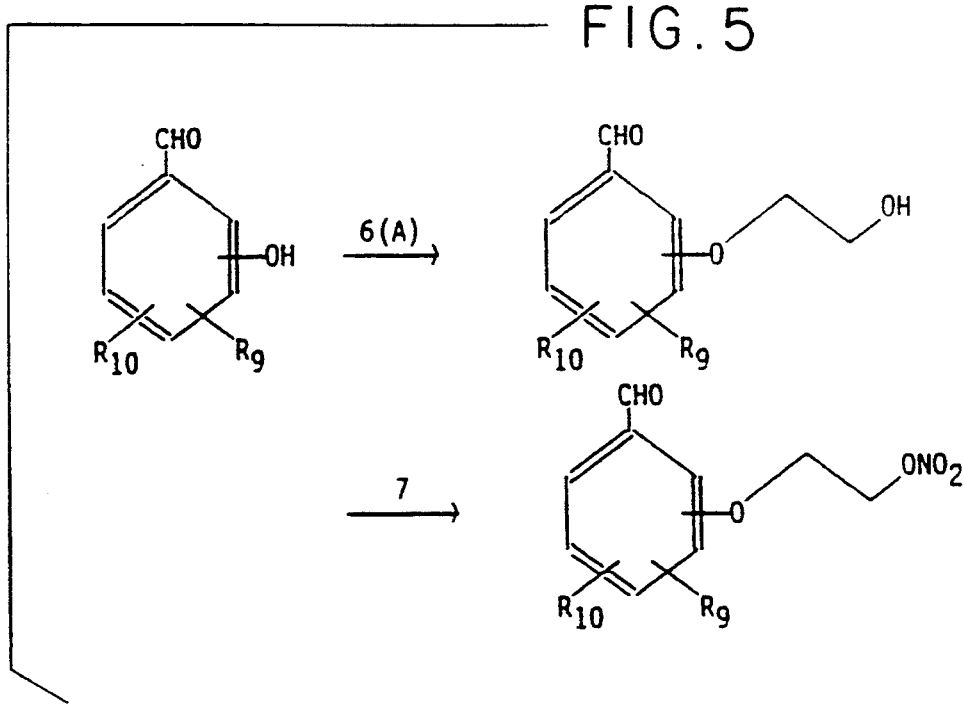
Figure 6:
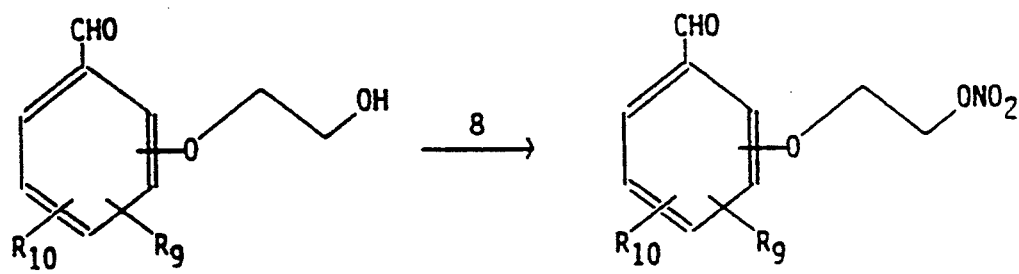
Figure 7:
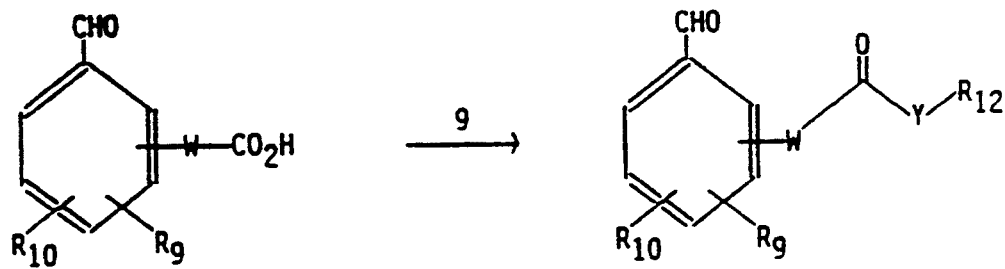

United States Patent [19]
Bron et al.

[11] Patent Number: 5,385,922
[45] Date of Patent: Jan. 31, 1995

[54] THIAZOLIDINE DERIVATIVES

[75] Inventors: Jan Bron, Giessenburg; Geert J. Sterk, Utrecht; Hendrik Timmerman, Voorschooten; Jan. F. Van Der Werf, Amsterdam, all of Netherlands

[73] Assignee: Cedona Pharmaceuticals B.V., Haarlem, Netherlands

[21] Appl. No.: 983,530

[22] PCT Filed: Sep. 3, 1991

[86] PCT No.: PCT/EP91/01663

§ 371 Date: Mar. 4, 1993

§ 102(e) Date: Mar. 4, 1993

[87] PCT Pub. No.: WO92/04337

PCT Pub. Date: Mar. 19, 1992

[30] Foreign Application Priority Data

Sep. 5, 1990 [NL] Netherlands .......................... 9001955

[51] Int. Cl.$^6$ .................. C07D 377/04; A61K 31/425
[52] U.S. Cl. ..................................... 514/365; 548/146; 548/200; 548/201
[58] Field of Search ...................... 548/146, 200, 201; 514/365

[56] References Cited

FOREIGN PATENT DOCUMENTS

| | | |
|---|---|---|
| 0083256 | 7/1983 | European Pat. Off. . |
| 0114270 | 8/1984 | European Pat. Off. . |
| 0207674 | 1/1987 | European Pat. Off. . |
| 0322068 | 6/1989 | European Pat. Off. . |
| 0362575 | 4/1990 | European Pat. Off. . |
| 3427241 | 2/1980 | Germany . |
| 3433383 | 3/1986 | Germany . |
| WO89/12627 | 12/1989 | WIPO . |

OTHER PUBLICATIONS

Fernandez, J. Med. Chem. 26 1317(1983).
Chemical Abstracts, vol. 107, No. 19, pp. 725, Abstract 176023b, Nov. 9, 1987.

*Primary Examiner*—Robert Gerstl
*Attorney, Agent, or Firm*—Jacobson, Price, Holman & Stern

[57] ABSTRACT

Thiazolidine derivatives containing at least one organic nitrate ester group have cardiovascular activity.

4 Claims, 2 Drawing Sheets

1

2

THIAZOLIDINE DERIVATIVES

The invention relates to novel thiazolidine derivatives having the formula 1, and their salts, in which formula
R1 represents H or 1-4C-alkyl,
R2 represents H, 1-6C-alkyl, 4-8C-cycloalkyl, phenyl-1-3C-alkyl or a group of the general formula 2,
wherein
R9, R10 and R11 simultaneously or separately represents H, 1-6C-alkyl, 1-6C-alkoxy, 4-8C-cycloalkyl, 4-8C-cycloalkoxy, F, Cl, Br, NO2, nitroxy-2-6C-alkoxy, nitroxy-4-8C-cycloalkoxy, nitroxy-1-2C-alkyl-4-8C-cycloalkyl-1-2C-alkoxy or a group

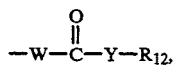

wherein
W represents a bond or a group —OCH2—,
Y represents an oxygen atom or an imino group and
R12 represents H, 1-4C-alkyl, 4-8C-cycloalkyl, nitroxy-2-6C-alkyl or nitroxy-4-8C-cycloalkyl,
R3 and R4 represents H or 1-4C-alkyl,
R5 represents H or a group

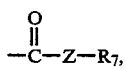

wherein
Z represents an oxygen atom or an imino group and
R7 represents H, 1-4C-alkyl, 4-8C-cycloalkyl, nitroxy-2-6C-alkyl, nitroxy-4-8C-cycloalkyl, nitroxy-1-2C-alkyl-4-8C-cycloalkyl-1-2C-alkyl or 4-nitroxy-2,6-dioxabicyclo[3.3.0]oct-8-yl, and
R6 represents H or a group —X—R8,
wherein
X represents carbonyl or sulfonyl and
R8 represents 1-4C-alkyl, 4-8C-cycloalkyl, nitroxy-2-6C-alkyl, nitroxy-4-8C-cycloalkyl, phenyl or 1-4C-alkylphenyl.

It has been found that these novel thiazolidine derivatives have outstanding properties as medicaments. The novel thiazolidine derivatives may be used, optionally symptomatically, in the treatment of pathological processes in mammals, especially man, where it is necessary, for example.
a. to increase the availability of oxygen to the tissues,
b. to protect the mucosa, for example the gastrointestinal mucous membrane, or
c. to intervene in the reproduction mechanisms of viruses.

By virtue of their pharmacological characteristics, the novel thiazolidine derivatives can be used in the case of
a. ischemic heart diseases (such as angina pectoris and latent ischemia),
b. cardiac decompensation, myocardial infarction or raised blood pressure (especially portal hypertension),
c. cerebral thrombosis and atherosclerosis,
d. vessel spasms and arrhythmia etc.,
e. disorders of the gastrointestinal tract, such as achalasia and irritable bowel syndrome, or
f. tardive dyskinesia.

The invention thus also relates to a medicament for the treatment of the above-mentioned disorders which contains, as active substance, a thiazolidine derivative having the formula 1 described above, or a salt thereof. The novel thiazolidine derivatives all contain one or more organic nitrate ester groups. Organic nitrate esters, such as glyceryl trinitrate and isosorbide dinitrate, have already been used medicinally for more than 100 years, and 50 years respectively, as vasodilators in, inter alia, angina pectoris. With regard to the manner in which vasodilation is effected by nitrate esters, it is postulated, inter alia, that this is caused, inter alia, by nitric oxide NO. It is known that endogenous NO can be liberated from endothelium cells on an intact vessel wall by specific mediators such as acetylcholine, bradykinin, serotonin, histamine and the like. This endogenous NO, which is also termed endothelium derived relaxing factor (EDRF), is alleged, in turn, to stimulate the enzyme guanylate cyclase in the adjacent smooth muscle cells. As a result, inter alia, of the increased concentrations of cyclic GMP, the existing balance in the vessel wall tension is disturbed, which, via a cascade of reactions, ultimately leads to relaxation of the smooth muscle cells in the vessel wall.

Organic nitrate esters are able to give rise to vasodilation even if the endothelial cell layer has been damaged or removed, which effect could be explained by direct formation of NO from these nitrate esters. It is alleged that sulphhydryl-containing endogenous compounds such as the amino acid cysteine play a role in this process, which presumably proceeds enzymatically. It is postulated that the pharmacodynamic effects of nitrate esters decrease in the course of time as a result of depletion of the said sulphhydryl compounds if treatment with nitrate esters is continued without a break. This phenomenon, which incidentally is reversible by temporarily stopping therapy, is termed nitrate tolerance.

Moreover, in the literature reference is made to the possibility that —SNO compounds instead of NO lead to relaxation. NO is then converted to RSNO by means of endogenous sulphhydryl compounds RSH. In this case also it is alleged that depletion or RSH can lead to nitrate tolerance.

Various approaches are described in the literature in order to prevent nitrate tolerance. Thus, it is alleged that the addition of high dosage (1-3 grams) of N-acetylcysteine to a glyceryl trinitrate therapy does not lead to tolerance but scientific opinions are divided in this regard. Moreover, in a U.S. patent application Ser. No. 89/02611 (WO 89/12627), hybrid compounds of angiotensin converting enzyme (ACE) inhibitors (agents which lower the blood pressure, such as captopril, which contains a —SH group) and NO are described. The S-ni-trosocaptopril described in this literature reference does indeed have an ACE-inhibiting effect comparable to that of captopril (IC50=about $10^{-9}$ M), but the relaxing effect via the NO portion in a rat aorta contracted using phenylephrine lies at a concentration which is about 100 times higher (IC50=about $10^{-7}$M). Therefore, in this example the desired combination of effects cannot be achieved in a single molecule. Moreover, the relaxing effects in this literature reference are a factor of 100-1000 times lower than those of the above-mentioned NO, glyceryl nitrate or sodium nitroprusside (NO-containing, that is to say $Na_2[Fe(CN)_5NO]$) in a comparable experimental set-up. Even if the relaxing effect were not subject to nitrate tolerance in the case of these compounds, the ACE-inhibiting effect would lead to a therapeutically inadmissible fall in the blood pressure at the dosages which are needed for nitrate-mediated relaxation. Yet another approach is described in EP 0,362,575. In this patent use is made of the hypothesis that endogenous S-containing amino acids, such as cysteine or methionine, play a role in the process which leads to vasodilation. The example described in this literature reference are to be regarded as hybrids of nitrate esters of low alkanolcarboxylic acids and previously mentioned endogenous unsubstituted or substituted amino acids, coupled to one another via a peptide compound. It is alleged that a nitrate activity can be achieved with high concentrations ($10^{-4}$M) of these compounds without the accompanying phenomenon of nitrate tolerance.

Hybrid compounds of nitrate esters are also described in, for example, EP 0,207,674, EP 0,114,270 DE 3,427,241, EP 0,083,256 and DE 3,433,383, wherein, in addition to the nitrate activity, another principle of action, such as blockade of β-adrenergic receptors or calcium ingress antagonism, is the aim of the compounds described.

Compounds which have ACE-inhibiting activity, such as captopril, are hybridised with NO as indicated above. ACE-inhibiting compounds usually consist of, for example, a dipeptide or tripeptide, one of the amino acids optionally being a L-proline derivative. In place of L-proline, thiazolidinecarboxylic acid has also been used in ACE-inhibitors.

Preferred compounds according to the invention are those of the general formula 1,
wherein
$R_1$ represents H,
$R_2$ represents H, 1–4C-alkyl, phenyl-1–2C-alkyl or a group of formula 2 according to claim 1,
wherein
$R_9$, $R_{10}$ and $R_{11}$ simultaneously or separately represent H, 1–6C-alkoxy, Cl, Br, $NO_2$, nitroxy-2–6C-alkoxy, nitroxy-1–2C-alkyl-4–8C-cycloalkyl-1–2C-alkoxy or a group

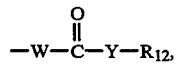

wherein
W represents a bond or a group —$OCH_2$—,
Y represents an oxygen atom or an imino group and $R_{12}$ represents H or nitroxy-2–6C-alkyl,
$R_3$ and $R_4$ represent H or methyl,
$R_5$ represents H or a group

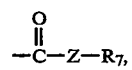

wherein
Z represents an oxygen atom or an imino group and
$R_7$ represents H, 1–4C-alkyl, nitroxy-2–4C-alkyl nitroxymethyl-4–8C-cycloalkylmethyl or 4-nitroxy-2,6-dioxabicyclo[3.3.0]oct-8-yl,
and
$R_6$ represents H or a group —X—$R_8$,
wherein
X represents carbonyl or sulfonyl and
$R_8$ represents 1–4C-alkyl, nitroxy-2–6C-alkyl, phenyl or 1–3C-alkyl-phenyl,
and their salts.

Particularly preferred compounds according to the invention are those of the general formula 1,
wherein
$R_1$ represents H,
$R_2$ represents phenylethyl or a group of formula 2 according to claim 1,
wherein
$R_9$, $R_{10}$ and $R_{11}$ simultaneously or separately represent H, methoxy or nitroxyethoxy,
$R_3$ and $R_4$ represent H,
$R_5$ represents H or a group

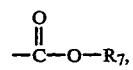

$R_7$ represents H or 4-nitroxymethylcyclohexylmethyl,
and
$R_6$ represents H,
and their salts.

Alkyl groups are straight-chain or branched.

4-Carboxy-2-[5-methoxy-2-methoxy-2-(2-nitroxyethoxy)phenyl]thiazolidine, 4-carboxy-2-[2-(2-nitroxyethoxy)phenyl)thiazolidine, 4-carboxy-2-[5-nitro-2-nitroxyethoxy)phenyl]thiazolidine, N-acetyl-2-(2-phenylethyl)-4-[(4-nitroxymethylcyclohexyl)methoxycarbonyl]thiazolidine and 2-[(2-nitroxyethoxy)-phenyl]thiazolidine oxalate hydrate and their salts are considered as of outstanding value.

Suitable salts include all salts with acids, particularly the pharmacologically-acceptable salts of inorganic and organic acids custumarily used in the pharmaceutical industry. Pharmacologically-unacceptable salts, which are, e.g., initially obtained as process products in preparing the compounds according to the invention on an industrial scale, are readily converted into pharmacologically-acceptable salts by conventional processess known to those skilled in the art. Examples of suitable salts are water-soluble and water-insoluble acid-addition salts, such as the hydrochloride, hydrobromide, hydroodide, phosphate, nitrate, sulfate, acetate, citrate, gluconate, benzoate, hibenzate, fendizoate, butyrate, sulfosalicylate, maleate, laurate, malate, fumarate, succinate, oxalate, tartrate, amsonate, metembonate, stearate, tosylate, 2-hydroxy-3-naphthoate, 3-hydroxy-2-naphthoate or mesylate.

The present invention describes completely novel organic nitrate esters which contain, as core, a thiazolidine structure and which are able, either by simple hydrolysis or by enzymatic conversion, to supply a —SH group, so that possible nitrate tolerance can be prevented. If the thiazolidine ring remains intact, ACE-inhibiting activity is possible. Both in vitro and in vivo the novel compounds described display a distinct effect which indicates lasting vasodilation.

The synthesis of the novel compounds takes place by methods known per se. A number of these syntheses are shown in the appended reaction schemes A–D. In these reaction schemes, the symbols have the same meaning as in formula 1, while HZ is an acid, such as hydrochloric acid, hydrogen bromide, hydrogen iodide, acetic acid, oxalic acid, maleic acid, methanesulphonic acid and the like.

REACTION SCHEME A

Reaction 1

Reaction 1 is preferably carried out in water or in a mixture of water and a water-miscible organic solvent which is inert under these conditions, such as methanol, ethanol, propan-2-ol, propan-1-ol, tetrahydrofuran, dioxane and the like.

The reactants can be mixed with one another in a molar ratio of one to one or using an excess of the mercaptoalkylamino compound.

The product from Reaction 1 can generally be obtained in high yield and in solid form, possibly as a mixture of dia(iso)stereomers as a result of the asymmetric C2 atom formed. Preferably, the solvents required for the reaction are freed from atmospheric oxygen by bubbling an inert gas such as nitrogen through the solvent.

Reaction 2

The acylation reaction (2) of the thiazolidine can be carried out in a solvent suitable for this purpose, such as water, tetrahydrofuran, dioxane, ethyl acetate, pyridine and the like, in the presence of a suitable base, such as sodium hydroxide, potassium carbonate, pyridine, 4-dimethylaminopyridine and the like.

The acylating reagent used can be an acid chloride or acid anhydride or a carboxylic acid, which can then be activated using a chloroformate, a carbodiimide and the like.

Reaction 3

If $R_5$ is a carboxylic acid group, this can be converted with the aid of known methods into an ester or an amide. The most suitable methods for this reaction are an acid-catalysed esterification or via activation of the carboxylic acid group with the aid of a chloroformate or a carbodiimide.

REACTION SCHEME B

Reaction 4

If $R_5$ is a carboxylic acid group, this can be converted with the aid of known methods into an ester or an amide. The most suitable methods for this reaction are an acid-catalysed esterification or via activation of the carboxylic acid group with the aid of a chloroformate or a carbodiimide.

Reaction 5

The acylation reaction (5) of the thiazolidine can be carried out in a solvent suitable for this purpose, such as water, tetrahydrofuran, dioxane, ethyl acetate, pyridine and the like, in the presence of a suitable base, such as sodium hydroxide, potassium carbonate, pyridine, 4-dimethylaminopyridine and the like.

The acylating reagent used can be an acid chloride or acid anhydride or a carboxylic acid which can then be activated using a chloroformate, a carbodiimide and the like.

REACTION SCHEME C1

Reaction 6

There are various methods for the synthesis of hydroxyalkoxybenzaldehydes.

Method A: reaction of, for example, a hydroxyalkylsulphonate or halogenoalkyl with a hydroxybenzaldehyde, or Method B: reaction of a hydroxybenzaldehyde with ethylene carbonate with the aid of catalysis by a quaternary ammonium compound.

Reaction 7

Formation of the nitrate ester of the reaction product from Reaction 6 can be carried out as described in the literature, but preferably using the acetic anhydride/nitric acid method.

REACTION SCHEME C2

Reaction 8

For reaction 8 the hydroalkoxybenzaldehyde is added slowly and at low temperature preferably between −20° C. and +5° C.) to absolute nitric acid.

Under these conditions, one or more nitrate esters are formed, n being zero, one or two. The various reaction products can be separated from one another with the aid of crystallisation and/or chromatographic techniques.

REACTION SCHEME D

Reaction 9

Reaction 9 is identical to Reaction 3 and W can be a bond or a group having the formula

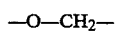

The following examples illustrate the preparation of the compounds of the invention.

EXAMPLE Ia 2-butyl-4-carboxythiazolidine 10 g of pentan-1-al were added to a vigorously stirred solution of 20 g of L-cysteine in 200 ml of $H_2O$. After 30 minutes, the solid substance was filtered off, washed with water and dried. Yield: 80%. Melting point: 169°–170° C.

NMR (DMSO-$d_6$): 0.86 ppm, t, J=5.9 Hz, 3.0 H, ($CH_3$); 1.04–2.06 ppm m, 6.0 H, (propylene); 2.58–3.32 ppm, m, 2.0 H ($CH_2$-thiazolidine); 3.29–4.17 ppm, m, 1.0 H ($CH_2$-thiazolidine); 7.10 ppm, broad signal, 2.2 H ($CO_2H+NH$).

EXAMPLE Ib

N-methylbenzenesulphonyl-2-butyl-4-carboxy-N-(4-methylbenzenesulphonyl)thiazolidine 1 equivalent of 4-methylbenzenesulphonyl chloride in tetrahydrofuran (100 ml) was added at 0° C. to a solution of 10 g of the compound from Example Ia and 10 g of $K_2CO_3$ in 200 ml of $H_2O$. After everything has been added, the solution was stirred for a further 60 minutes at room temperature and then concentrated under reduced pressure. The solution, which was still basic, was extracted twice with 200 ml of ethyl acetate, which was discarded. The aqueous solution was acidified with concentrated hydrochloric acid and extracted three times with ethyl acetate. The organic fractions were dried over $MgSO_4$ and evaporated. Yield 65%. Melting point: oil.

NMR (CDCl$_3$): 0.86 ppm, t, J=5.9 Hz, 3.0 H (—C—$CH_3$); 1.08–2.24 ppm, m, 6.0 H [($CH_2$)$_3$]; 2.43 ppm, s, 3.0 H (tosyl/$CH_3$); 2.07–3.5 ppm, m, 2.0 H ($CH_2$ thiazolidine); 5.58–6.10 ppm, m, 2.0 H (2×CH thiazolidine); 7.14–7.90 ppm, 4.0 H (arom. H), 10.10 ppm, s, 1.0 H ($CO_2H$).

EXAMPLE I

2-Butyl-N-(4-methylbenzenesulphonyl)-4-[(5-nitroxyisosorbide)carbonyl]thiazolidine 1 g of dicyclohexylcarbodiimide was added at 0° C. to a solution of 2.2 g of the compound from Example Ib and 1.19 g of isosorbide 5-mononitrate in 100 ml of ethyl acetate. After everything had been added, the solution was stirred for a further 30 minutes at 0° C. and then for 2 hours at room temperature. After filtration, the solution was washed successively with dilute hydrochloric acid and aqueous sodium carbonate. After drying over $MgSO_4$, the solution was evaporated and the residue purified by column chromatography. Yield 60%. Empirical formula $C_{21}H_{28}N_2O_9S_2$. Molecular weight 516.64. Melting point 114°–115° C. (dichloromethane/petroleum ether 60/80). TLC system: diethyl ether. $R_f$ 0.27. Mass spectrum, calculated 516.64, found 516.64.

NMR data ($CDCl_3$): 0.86 ppm, t, J=5.9 Hz, 3.0 H (aliphatic $CH_3$); 2.76–3.58 ppm, m, 2.0 H ($CH_2$ thiazolidine); 3.76–4.18 ppm, m, 4.0 H (2×$CH_2$ of isosorbide); 4.44–4.68 ppm, m, 2.0 H (2×CH of isosorbide); 4.78–5.06 ppm, m, 2.0 H (CH or isosorbide+CH thiazolidine); 5.22–5.50 ppm, m, 2.0 H (CH of isosorbide+CH of thiazolidine); 7.18–7.80 ppm, m, 4.0 H (arom. H).

EXAMPLE IIa

N-benzoyl-2-butyl-4-carboxythiazolidine

Synthesized analogously to Example Ib from 10 g of the compound from Example Ia and 1 equivalent of benzoyl chloride. Purification by column chromatography (silica gel). Yield 78%.

NMR ($CDCl_3$): 0.48–2.30 ppm, m, 9.0 H (butyl group); 3.00–3.70 ppm, m, 2.0 H ($CH_2$ thaizolidine); 4.45–5.60 ppm, m, 2.0 H (2×CH thiazolidine); 7.20–8.13 ppm, m, 5.0 H (arom. H); 10.30 ppm, s, 1.2 H ($CO_2H$).

EXAMPLE II

N-benzoyl-4-[(5-nitroxyisosorbide)carbonyl]-2-butyl-thiazolidine

Synthesized analogously to Example I from 2.2 g of the compound from Example IIa and 1.0 g of isosorbide 5-mononitrate. Purified by column chromatography (silica gel, ether:petroleum ether/4:1). Yield 45%. Empirical formula $C_{21}H_{26}N_2O_8S$. Molecular weight 466. Melting point: oil. TLC system: diethyl ether. $R_f$ 0.74.

NMR data ($CDCl_3$): 0.68–2.50 ppm, m, 9.0 H (butyl group); 3.10–3.54 ppm, m, 2.0 H ($CH_2$ thiazolidine); 3.80–4.20 ppm, m, 4.0 H (2×$CH_2$ isosorbide); 4.42–4.61 ppm, m, 2.0 H, (CH thiazolidine and CH isosorbide); 5.18–5.30 ppm, m, 2.0 H (CH thiazolidine and CH isosorbide); 7.44 ppm, s, 5.0 H (arom. H).

EXAMPLE IIIa 4-carboxy-5,5-dimethyl-2-pentylthiazolidine 4 g of hexanal were added to a vigorously stirred solution of 9 g of D-penicillamine in 100 ml of $H_2O$. After stirring for 30 minutes, the solid substance was filtered off, washed successively with water and diethyl ether and dried. Yield 60%.

NMR DMSO-$d_6$: 0.84 ppm, t, J=6.5 Hz, 3.0 H ($CH_3$) 1.06–2.04 ppm, m, 12.6 H (($CH_2$)$_3$+C($CH_3$)$_2$; 3.40 ppm, s, 1.0 H (CH—$CO_2$); 4.46 ppm, t, J=7.0 H, 1.0 H (CH).

EXAMPLE IIIb

N-benzoyl-4-carboxy-5,5-dimethyl-2-pentylthiazolidine

Synthesized analogously to Example Ib from 4 g of the compound from Example IIIa and 1 equivalent of benzoyl chloride. Purified by column chromatography (silica gel). Yield 63%. Melting point: oil. TLC system: diethyl ether. $R_f$ 0.62.

NMR $CDCl_3$): 0.64–2.66 ppm, m, 15.0 H (butyl+2×$CH_3$); 4.20 ppm, broad signal, 0.9 H (CH); 5.50 ppm, broad signal, 1.0 H (CH); 7.30–8.20 ppm, m, 5.0 H (arom. H); 9.24 ppm, s, 1.0 H ($CO_2H$).

EXAMPLE III

N-benzoyl-2-butyl-5,5-dimethyl-4-[(5-nitroxyisosorbide)carbonyl]thiazolidine

Synthesized analogously to Example I from 1 g of the compound from Example IIIb and 1 equivalent of isosorbide 5-nitrate and purified by preparative TLC (silica gel, $CHCl_3$). Empirical formula $C_{24}H_{32}N_2O_8S$. Molecular weight 508.19. Melting point: oil. TLC system: ether/petroleum ether 60–80/1:1. $R_f$ 0.23. Mass spectrometry, calculated 508,1848, found 508,1879.

NMR data ($CDCl_3$): 0.60–2.65 ppm, m, 15.0 H (butyl+2×$CH_3$); 3.62–4.30 ppm, m, 5.0 H (2×$CH_2$ isosorbide+CH thiazolidine) 4.37–4.70 ppm, m, 1.0 H (CH isosorbide); 4.79–5.04 ppm, m, 1.0 H (CH isosorbide); 5.16–5.60 ppm, m, 3.0 H (2×CH isosorbide+CH thiazolidine); 7.38 ppm, m, 5.0 H (arom. H).

EXAMPLE IVa

2-Butyl-4-carboxy-5,5-dimethyl-N-(4-methylbenzenesulphonyl)thiazolidine

Synthesized analogously to Example Ib from 4 g of the compound from Example IIIa and 1 equivalent of p-toluenesulphonyl chloride. Purified by column chromatography silica gel, ethyl acetate). Yield 67% Melting point: oil. TLC: ethyl acetate. $R_f$ 0.75.

EXAMPLE IV

2-Butyl-5,5-dimethyl-N-(4-methylbenzenesulphonyl)-4-[(5-nitroxyisosorbide)carbonyl]thiazolidine Synthesized analogously to Example I from 3 g of the compound from Example IVa and 1 equivalent of isosorbide 5-nitrate. Purified by column chromatography (silica gel, diethyl ether). Yield 54%. Empirical formula $C_{24}H_{34}N_2O_9S_2$. Molecular weight 558.07. Melting point 89°–91° C. TLC system: ether. $R_f$ 0.82.

Mass spectrometry, calculated: minus $NO_2$:M=512,1777, found M=512,1756.

NMR data ($CDCl_3$): 0.85 ppm, t, J=6.0 Hz, 3.0 H ($CH_3$) 1.06–2.36 ppm, m, 12.0 H (C($CH_3$)$_2$+($CH_2$)$_3$); 2.43 ppm, s, 3.0 H (tosyl $CH_3$); 3.73–4.14 ppm, m, 4.0 H (2×$CH_2$ isosorbide); 4.24–4.48 ppm, m, 2.0 H (2×CH isosorbide); 4.80–5.08 ppm, m, 2.0 H (CH isosorbide)+CH thiazolidine); 5.14–5.47 ppm, m, 2.0 H (CH isosorbide+CH thiazolidine) 7.18–7.79 ppm, m, 4.0 H (arom. H).

EXAMPLE Va

4-[(2-Nitroxyethyl)aminocarbonyl]benzaldehyde 0.1 mol of ethyl chloroformate was added at 0° C. to a solution of 0.1 mol of 4-carboxybenzaldehyde and 0.12 mol of triethylamine in $CH_2Cl_2$. After stirring for 30 minutes, a solution of 0.1 mol of aminoethyl nitrate×HNO$_3$ and 0.12 mol of triethylamine in CH$_2$Cl$_2$ was added. After stirring for 30 minutes, the solution was washed successively with dilute hydrochloric acid and aqueous sodium carbonate.

The solution was dried over MgSO$_4$ and evaporated. The addition of diethyl ether to the residue caused crystallisation. Yield 71%. Melting point 77°–79° C.

$^1$H NMR (CDCl$_3$): 3.88 ppm, q, J=5.0 Hz, 2.0 H (CH$_2$N); 4.71 ppm, t, J=5.0 Hz, 2.0 H (CH$_2$O); 7.00 ppm, bs, 1.0 (NH); 7.95 ppm, s, 4.0 H (arom. H); 10.80 ppm, s, 1.0 H (CHO).

EXAMPLE V

4-Carboxy-2-{4-[(2-nitroxyethyl)aminocarbonyl]phenyl}thiazolidine

Water was added to a stirred mixture of 3 g of cysteine and 5 g of the compound from Example Va in 100 ml of THF until everything had dissolved. The solution was then concentrated under reduced in order to remove THF. The solid substance which formed was washed with water and dried. Yield 82%. Empirical formula C$_{13}$H$_{15}$N$_3$O$_6$S. Molecular weight 341. Melting point: 128°–130° C.

NMR data (DMSO): 2.96–4.30 ppm, m, 5.0 H (CH$_2$N+SCH$_2$CHN); 4.68 ppm, t, J=5.0 Hz, 2.0 H (CH$_2$O); 5.68 ppm, d, J=19.8 Hz, 1.0 H (phenyl-CH); 7.43–7.97 ppm, m, 4.0 H (arom. H); 8.75 ppm, s, 1.0 H (CO$_2$H).

EXAMPLE VI

N-acetyl-4-carboxy-2-(2-carboxyphenyl)thiazolidine

A solution of 6 of 2-carboxybenzaldehyde and 4.8 g of cysteine in 100 ml of water was stirred for 15 minutes. After adding 10 g of K$_2$CO$_3$, the solution was cooled to 0° C. and a solution of 8 g of acetic anhydride in THF was added. After everything had been added, the solution was stirred for a further 15 minutes at 0° C. and then for 1 hour at room temperature. The solution was concentrated under reduced pressure in order to evaporate THF, acidified to pH 1–2 with sulphuric acid and extracted with ethyl acetate. After drying over MgSO$_4$ and evaporation of the solvent, the residue was crystallised from ethyl acetate/diethyl ether. Yield 22%.

$^1$H NMR (CDCl$_3$/DMSO): 1.92 ppm, d, J=5.4 Hz, 3.0 H (CH$_3$); 2.31 ppm, s, 1.0 H (CH); 2.80–3.62 ppm, m, 2.0 H (CH$_2$); 4.37–4.96 ppm, m, 1.0 H (SCHN); 7.02–8.50 ppm, m, 4.0 H (arom. H).

EXAMPLE VI

N-acetyl-2-(2-carboxyphenyl)-4-[(2-nitroxyethyl)aminocarbonyl]thiazolidine

The compound was synthesized from 1.5 g of the compound from Example VIa and 1.73 g of aminoethyl nitrate. HNO$_3$ as described in Example Va. The product was crystallised from ethyl acetate/petroleum ether 60/80. Yield 40%. Empirical formula C$_{15}$H$_{17}$N$_3$O$_7$S. Molecular weight 383. Melting point 148°–150° C. TLC system: ethyl acetate. R$_f$ 0.65.

NMR data (CDCl$_3$/DMSO): 1.84–2.07 ppm, m, 2.0 H (SCH$_2$); 3.00–3.26 ppm, m, 4.0 H (CH$_3$+CHCO); 3.44–3.82 ppm, m, 2.0 H (CH$_2$N); 4.46–4.80 ppm, m, 3.1 H (CH$_2$O+SCH); 7.20–7.60 ppm, m, 2.0 H (arom. H) 8.26–8.80 ppm, m, 2.0 H (arom. H).

EXAMPLE VII

4-Ethoxycarbonyl-2-{4-[(2-nitroxyethyl)aminocarbonyl]phenyl}thiazolidine×HCl 5 g of thionyl chloride were added at −15° C. to 200 ml of ethanol, followed by the addition of 5 g of the compound from Example V and the mixture was allowed to stand overnight. After removal of the solvent, the residue was dissolved in water with excess sodium carbonate, the aqueous phase was extracted with ether and the ether phase was dried over sodium sulphate. Hydrochloric acid was added to the ether phase and the precipitate was filtered off and recrystallised from ethanol/ether. Yield: 40%. Empirical formula C$_{15}$H$_{20}$ClN$_3$O$_6$S. Molecular weight 405.5. Melting point 107°–110° C. TLC system: ethyl acetate. R$_f$ 0.66.

NMR data (DMSO): 1.24 ppm, t, J=7.0 Hz, 3.0 H (CH$_3$); 3.22–4.80 ppm, m, 4.9 H (NCH$_2$+CHCH$_2$); 4.21 ppm, q, J=7.0 Hz, 2.0 H (CH$_2$ ethyl) 4.55–4.88 ppm, m, 2.0 H (CH$_2$ONO$_2$); 5.88 ppm, s, 0.9 H (SCH); 7.50–8.10 ppm, m, 6.0 H (arom. H+NH$_2$); 8.83 ppm, bs, 1.0 H (CONH).

EXAMPLE VIIIa

N-acetyl-4-carboxy-2-phenylthiazolidine 10 g of acetic anhydride were added slowly at 0° C. to a solution of 15 g of 4-carboxy-2-phenylthiazolidine in H$_2$O while the pH was kept at 9–10. After everything had been added, the solution was stirred for a further 60 minutes. H$_2$SO$_4$ was added to pH=1. The precipitate was filtered off, dried and crystallised from ethyl acetate/petroleum ether 60/80. Yield 74%. Melting point 129°–132° C.

$^1$H NMR (CDCl$_3$): 1.97 ppm, s, 2.9 H (CH$_3$); 3.25–3.56 ppm, m, 2.0 H (CH$_2$); 5.06 ppm, t, J=6.9 Hz, 1.0 H (CHCO$_2$); 6.04 ppm, s, 0.9 H (SCH); 7.14–7.34 ppm, m, 5.0 H (arom. H); 8.60 ppm, bs, 1.3 H (CO$_2$).

EXAMPLE VIII

N-acetyl-2-phenyl-4-[(2-nitroxyethyl)aminocarbonyl]thiazolidine

Synthesized from 5 g of the compound from Example VIIIa as described in Example Va. Yield 49%. Empirical formula C$_{14}$H$_{17}$N$_3$O$_5$S. Molecular weight 339. Melting point 103°–105° C. TLC system: ethyl acetate. R$_f$ 0.61.

NMR data (CDCl$_3$-DMSO): 1.98 ppm, s, 2.9 H (CH$_3$); 2.96–3.92 ppm, m, 4.2 H (CHCH$_2$+NCH); 4.57 ppm, t, J=5.3 Hz, 2.0 H (CH$_2$ONO$_2$); 5.06 ppm, t, J=5.5 Hz, 1.0 H (NH); 5.98 ppm, s, 0.9 H (SCH); 7.18–7.55 ppm, m, 5.1 H (arom. H).

EXAMPLE IXa 2-(2-Formylphenoxy)-N-(2-nitroxyethyl)acetamide

Prepared from 10 g of 2-formylphenoxyacetic acid as described in Example Va. Yield 70% Melting point 99°–101° C.

EXAMPLE IX

4-Carboxy-2-{2-[(2-nitroxyethyl)aminocarbonylmethoxyl]phenyl}thiazolidine

THF was added to a mixture of 5 g of the compound from Example IXa and 3 g of cysteine in water until a clear solution resulted. The solution was then concentrated under reduced pressure until a precipitate formed. This precipitate was filtered off and dried.

Yield 11%. Empirical formula $C_{14}H_{17}N_3O_7S$. Molecular weight 371. Melting point 99°–103° C. TLC system: methanol. $R_f$ 0.72.

NMR data (DMSO): 2.82–4.30 ppm, m, 5.0 H ($CONCH_2+CHCH_2$); 4.45–4.80 ppm, m, 4.0 H ($2\times CH_2O$); 5.80 ppm, 6.01 ppm, two singlets, 1.0 H (SCH); 6.80–7.80 ppm, m, 5.0 H (arom. H+NH); 8.30 ppm, bs, 1.0 H (HN); 11.00 ppm, bs, 1.0 H ($CO_2H$).

EXAMPLE Xa

4-Formyl-2-methoxyphenoxyacetic acid

A solution of 30.4 g of 4-hydroxy-3-methoxybenzaldehyde, 31.2 g of chloroacetic acid and 34 g of potassium hydroxide in 300 ml of water was refluxed for 7 hours. After cooling, hydrochloric acid was added and the precipitate was filtered off and dried. Yield 57%.

$^1$H NMR (DMSO): 3.86 ppm, s, 3.0 H ($OCH_3$); 4.83 ppm, s, 1.9 H ($OCH_2$); 7.06 ppm, d, J=8.0 Hz, 1.0 H (arom. H); 7.36–7.66 ppm, m, 2.1 H (arom. H); 9.84 ppm, s, 1.0 H (CH).

EXAMPLE Xb

4-Formyl-2-methoxyphenoxy-N-(2-nitroxyethyl)acetamide

Prepared from 10 g of the compound from Example Xa and 8.1 g of aminoethyl nitrate $\times HNO_3$ as described for the compound of Example IXa. Yield 73%. Melting point 117°–120° C.

$^1$H NMR ($CDCl_3$): 3.71 ppm, q, J=5.3 Hz, 2.0 H ($NCH_2$); 3.96 ppm, s, 3.0 H ($OCH_3$); 4.47–4.70 ppm, m, 4.0 H ($2\times OCH_2$); 6.86–7.54 ppm, m, 4.0 H (arom. H+NH); 9.84 ppm, s, 1.0 H (CH).

EXAMPLE X

4-Carboxy-2-{3-methoxy-4-[(2-nitroxyethyl)aminocarbonylmethoxy]phenyl}thiazolidine Prepared from 9 g of the compound from Example Xb and 4.9 g of cysteine as described in Example IX. Yield 60. Empirical formula $C_{15}H_{19}N_3O_8S$. Molecular weight 401. Melting point 151°–152° C. TLC system: methanol. $R_f$ 0.51.

NMR data ($CDCl_3$): 2.96–3.34 ppm, m, 2.0 H ($SCH_2$); 3.48 ppm, q, J=7.0 Hz, 2.0 H ($NCH_2$); 3.70–4.70 ppm, m, 8.0 H ($CHCO_2+OCH_3+2\times OCH_2$); 5.42 ppm, 5.58 ppm, two singlets, 1.0 H (SCH); 6.71–7.28 ppm, m, 4.0 H (arom. H+NH); 8.18 ppm, 1.0 H (NH).

EXAMPLE XI

4-Ethoxycarbonyl-2-{[3-methoxy-4-(2-nitroxyethyl)aminocarbonylmethoxy]phenyl}-thiazolidine hydrochloride Thionyl chloride (5 g) and the compound from Example X (3 g) were added successively at −15° C. to 200 ml of ethanol. After standing overnight, the solution was evaporated and the residue dissolved in water, sodium carbonate was added to pH=10 and the resulting mixture was extracted with ethyl acetate. After drying over magnesium sulphate, hydrochloric acid was added and the precipitate was filtered off and crystallised from ethanol/ether. Yield 45%. Empirical formula $C_{17}H_{24}ClN_3O_8S$. Molecular weight 465.5. Melting point 127°–130° C. TLC system: ethyl acetate. $R_f$ 0.58.

NMR data (DMSO): 1.29 ppm, t, J=7.0 Hz, 3.0 H ($CCH_3$); 2.60–2.96 ppm, m, 1.0 H ($CHCO_2$); 3.34–3.68 ppm, m, 4.0 H ($2\times CH_2$); 4.88 ppm, s, 3.0 H ($OCH_3$); 4.28 ppm, q, J=7.0 Hz, 2.0 H (ester $CH_2$); 4.49–5.05 ppm, m, 5.0 H ($2\times CH_2$, CH); 5.85 ppm, s, 1.0 H (phenyl-CH); 6.88–7.30 ppm, m, 2.0 H (arom. H); 7.45–7.67 ppm, m, 1.0 H (arom. H); 8.40 ppm, bs, 1.0 H (CONH); 14.00 ppm, bs, 2.0 H (NHHCl).

EXAMPLE XIIa

3-Ethoxy-2-(hydroxyethoxy)benzaldehyde

A mixture of 40 g of 3-ethoxysalicylaldehyde, 22 g of ethylene carbonate and 40 g of tetraethylammonium bromide was heated at 140° C. for 4 hours. After cooling to room temperature, ethyl acetate was added to the reaction mixture, the solid substance was filtered off, the filtrate was washed with water and the organic phase was dried over magnesium sulphate and evaporated. The residue was distilled under reduced pressure. Yield 70%. Boiling point 0.1 140°–145° C.

$^1$H NMR ($CDCl_3$): 1.50 ppm, t, J=7.0 Hz, 3.0 H ($CH_3$); 3.77–4.40 ppm, m, 7.0 H ($3\times CH_2$, OH); 6.90–7.53 ppm, m, 3.0 H (arom. H); 10.32 ppm, s, 0.9 H (CH).

EXAMPLE XIIb

3-Ethoxy-2-(2-nitroxyethoxy)benzaldehyde

A mixture of 2 ml of nitric acid and 5 ml of acetic anhydride was added at 0° C. to a solution of 5 g of the compound from Example XIIa in ethyl acetate. After stirring for 5 minutes, 100 ml of water were added to the reaction mixture and the resulting mixture was stirred for a further 30 minutes. The organic phase was washed with aqueous sodium carbonate, dried over magnesium sulphate and evaporated. Yield 70%.

$^1$H NMR ($CDCl_3$): 1.46 ppm, t, J=7.0 Hz, 3.0 H ($CH_3$); 4.13 ppm, q, J=7.0 Hz, 2.0 H (ethyl-$CH_2$); 4.38–4.63 ppm, m, 2.0 H ($CH_2CONO_2$); 4.82–5.00 ppm, m, 2.0 H ($CH_2ONO_2$); 7.04–7.54 ppm, m, 3.0 H (arom. H); 10.44 ppm, s, 0.9 H (CH).

EXAMPLE XII

4-Carboxy-2-[3-ethoxy-2-(2-nitroxyethoxy)phenyl]-thiazolidine

Prepared from the compound from Example XIIb and cysteine as described in Example V. Yield 40%. Empirical formula $C_{14}H_{18}N_2O_7S$. Molecular weight 358. Melting point 124°–125° C. TLC system: methanol:ethyl acetate:acetic acid/5:5:1. $R_f$ 0.72.

NMR data (DMSO): 1.33 ppm, t, J=7.0 Hz, 3.0 H ($CH_3$); 2.82–3.53 ppm, m, 2.0 H ($SCH_2$); 3.70–4.44 ppm, m, 5.0 H ($2\times$phenyl-$OCH_2$, $CHCO_2$); 4.71–4.96 ppm, m, 2.0 H ($CH_2O-NO_2$); 5.80 ppm, J=19.8 Hz, 1.0 H (phenyl-CH); 6.80–7.23 ppm, m, 3.0 H (arom. H); 14.00 ppm, bs, 1.8 H ($CO_2H$, NH).

EXAMPLE XIIIa 4-(2-Hydroxyethoxy)benzaldehyde

Synthesized from 30 g of 4-hydroxybenzaldehyde, 21 g of ethylene carbonate and 62 g of tetraethylammonium bromide as described in Example XIIa. Purified by distillation (boiling point 0.1 140°–150° C.). Yield 66%.

$^1$H NMR ($CDCl_2$): 2.73 ppm, bs, 0.9 H (OH); 3.87–4.29 ppm, m, 4.0 H ($CH_2CH_2$); 6.99 ppm, d, J=8.6 Hz, 2.0 H ($2\times$arom. H); 7.81 ppm, d, J=8.6 Hz, 2.0 H ($2\times$arom. H); 9.84 ppm, s, 0.9 H (CH).

EXAMPLE XIIIb

4-(2-Nitroxyethoxy)benzaldehyde

Prepared from 25 g of the compound from Example XIIIa, 19 ml of nitric acid and 50 ml of acetic anhydride in ethyl acetate as described for the compound of Example XIIb. Purified by chromatography (silica, $CH_2Cl_2$). Yield 50%.

$^1$H NMR ($CDCl_2$): 4.35 ppm, t, J=4.5 Hz, 2.0 H (phenyl-$OCH_2$); 4.86 ppm, t, J=4.5 Hz ($CH_2ONO_2$); 7.01 ppm, d, J=8, 6 Hz, 2.0 H (2×arom. H); 7.85 ppm, d, J=8.6 Hz, 2.0 H (2×arom. H); 9.89 ppm, s, 0.9 H (CH).

EXAMPLE XIII

4-Carboxy-2-[4-(2-nitroxyethoxy)phenyl]thiazolidine

A solution of 15 g of cysteine in water was added to a solution of 15 g of the compound from Example XIIIb in THF. Additional THF was added until the solution became virtually clear. The solution was filtered and concentrated in vacuo. The solid substance was filtered off and dried. The dried precipitate was refluxed in THF for 20 minutes and, after cooling, the solid substance was filtered off and dried. Yield 15%. Empirical formula $C_{12}H_{14}N_2O_6S$. Molecular weight 314. Melting point 139°–141° C. TLC system: ethyl acetate:methanol:acetic acid/20:4:1. $R_f$ 0.55.

NMR data (DMSO): 2.94–3.53 ppm, m, 2.0 H ($SCH_2$); 3.76–4.01 ppm, m, 0.5 H (0.5×$CHCO_2$); 4.17–4.42 ppm, m, 2.5 H (0.5×$CHCO_2$+phenyl-$OCH_2$); 4.77–5.02 ppm, m, 2.0 H ($CH_2ONO_2$); 5.52 ppm, d, J=12.9 Hz, 1.0 H (phenyl-CH); 6.82–7.07 ppm, m, 2.0 H (2×arom. H); 7.27–7.58 ppm, m, 2.0 H (2×arom. H).

EXAMPLE XIVa

2-(2-Hydroxyethoxy)-3-methoxybenzaldehyde

Prepared as described in example XIIa. Yield 70%. Boiling point 0.1 140° C.

$^1$H NMR ($CDCl_3$): 3.21 ppm, t, J=5.8 Hz, 0.9 H (OH); 3.79–4.38 ppm, m, 7×OH ($CH_2CH_2$, $CH_3$); 7.07–7.58 ppm, m, 3.0 H (arom. H); 10.34 ppm, s, 0.9 H (CH).

EXAMPLE XIVb

3-Methoxy-2-(2-nitroxyethoxy)benzaldehyde

Prepared as described in Example XIIb. Purified by chromatography (silica, ethyl acetate:petroleum ether 60–80/2:3). Crystallised from ethyl acetate/petroleum ether 60–80. Yield 50%. Melting point 70°–71° C.

$^1$H NMR ($CDCl_3$): 3.90 ppm, s, 3.0 H ($CH_3$); 4.37–4.56 ppm, m, 2.0 H ($OCH_2$); 4.74–4.95 ppm, m, 2.0 H ($CH_2ONO_2$); 7.14–7.56 ppm, m, 3.0 H (arom. H); 10.44 ppm, s, 1.0 H.

EXAMPLE XIV

4-Carboxyl-2-[3-methoxy-2-(2-nitroxyethoxy)phenyl]-thiazolidine

A solution of 1.0 g of the compound from Example XIVb in ethanol was added to a solution of 1.5 g of cysteine in $H_2O$. The mixture was stirred for 1 hour at room temperature, after which it was concentrated under reduced pressure. The resulting mixture was stirred for a further 30 minutes and decanted. The precipitate was treated with methanol and stirred for 30 minutes, after which the previously decanted solution was added again. The resulting solution was stirred for 1 hour. The precipitate was filtered off and washed with water and ether. Yield 60%. Empirical formula $C_{13}H_{16}N_2O_7S$. Molecular weight 344. Melting point 113°–115° C. TLC system: ethyl acetate:methanol:acetic acid/20:4:1. $R_f$ 0.58.

NMR data (DMSO): 2.92–3.56 ppm, 1.9 H ($SCH_2$); 3.76–4.02 ppm, m, 3.4 H ($OCH_3$+0.4×$CHCO_2$); 4.12–4.44 ppm, m, 2.5 H ($CH_2CONO_2$+0.5×$CHCO_2$); 4.74–5.01 ppm, m, 2.0 H ($CH_2ONO_2$); 5.85 ppm, d, J=19 Hz, 1.0 H (SCHN); 6.97–7.30 ppm, m, 3.4 H (arom. H+0.4×NH); 13.40 ppm, bs, 0.5 H (0.5×NH).

EXAMPLE XVa

2-(2-Hydroxyethoxy)-5-methoxybenzaldehyde

Prepared as described in Example XIIa from 5-methoxysalicylaldehyde. Purified by chromatography (silica, ethyl acetate). Yield 70%. Melting point 68°–72° C.

$^1$H NMR ($CDCl_3$): 2.50 ppm, bs, 1.0 H (OH); 3.80 ppm, s, 3.0 H ($CH_3$); 3.90–4.34 ppm, m, 4.0 H ($CH_2CH_2$); 6.87–7.40 ppm, m, 3.0 H (arom. H); 10.50 ppm, s, 0.9 H (CHO).

EXAMPLE XVb

5-Methoxy-2-(2-nitroxyethoxy)benzaldehyde

Prepared from the compound from Example XVa as described in example XIIb. Purified by chromatography (silica, ethyl acetate:petroleum ether 60–80/1:1). Yield 81%.

$^1$H NMR ($CDCl_3$): 3.80 ppm, s, 3.0 H ($CH_2$); 4.24–4.45 ppm, m, 1.9 H ($CH_2CONO_2$); 4.79–4.99 ppm, m, 1.9 H ($CH_2ONO_2$); 6.84–7.40 ppm, 3.0 H (arom. H); 10.41 ppm, s, 1.0 H (CHO).

EXAMPLE XV

4-Carboxy-2-[5-methoxy-2-(2-nitroxyethoxy)phenyl]-thiazolidine

Prepared from the compound from Example XVb as described in Example XIV. Yield 40%. Empirical formula C13H16N2O7S. Molecular weight 344. Melting point 110°–112° C. TLC system: ethyl acetate:methanol:acetic acid/8:4:1. $R_f$ 0.45.

NMR data (DMSO): 2.80–3.60 ppm, m, 2.0 H ($SCH_2$); 3.64–4.40 ppm, m, 6.0 H ($CH_3$, $CH_2CONO_2$, $CHCO_2$); 4.77–5.00 ppm, m, 2.0 H ($CH_2ONO_2$); 5.74 ppm, d, J=16.0 Hz, 1.0 H (SCH); 6.68–7.28 ppm, m, 3.0 H (arom. H); 9.00 ppm, bs, 2.0 H (NH, OH).

EXAMPLE XVIa

2-(2-Hydroxyethoxy)benzaldehyde

Synthesized as described in Example XIIa from salicylaldehyde. Yield 70%. Boiling point 141°–144° C. (0.1 mm Hg).

$^1$H NMR ($CDCl_3$): 2.90 ppm, t, J=5.0 Hz, 1.0 H (OH); 3.96–4.23 ppm, m, 4.0 H (2×$CH_2$); 6.90–7.90 ppm, m, 4.0 (arom. H); 9.94 ppm, s, 0.9 H (CH).

EXAMPLE XVIb

2-(2-Nitroxyethoxy)benzaldehyde

Prepared as described in Example XIIb from the compound from Example XVIa. Yield 80%.

$^1$H NMR ($CDCl_3$): 4.39 ppm, t, J=4.5 Hz, 2.0 H ($OCH_2$); 4.90 ppm, t, J=4.5 Hz, 2.0 H ($CH_2ONO_2$); 6.90–7.92 ppm, m, 4.0 H (arom. H); 10.42 ppm, s, 1.0 H (CH).

EXAMPLE XVI

4-Carboxy-2-[2-(2-nitroxyethoxy)phenyl]thiazolidine

A solution of 5 g of the compound from Example XVIb in tetrahydrofuran was added to a solution of 5 g of cysteine in water. Tetrahydrofuran was added to the mixture until a clear solution resulted. This solution was concentrated in vacuo. The resulting mixture was cooled in ice and stirred for 30 minutes. The solid substance was filtered off and washed thoroughly with water and ether. The compound was recrystallised from water/THF. Yield 40%. Empirical formula $C_{12}H_{14}N_2O_6S$. Molecular weight 314. Melting point 118°–120° C. (decomposition). TLC system: methanol. $R_f$ 0.53.

NMR data (DMSO): 2.79–3.53 ppm, m, 2.0 H ($SCH_2$); 3.71–4.52 ppm, m, 3.0 H ($CH_2CONO_2$, $CHCO_2$); 4.73–5.06 ppm, m, 2.0 H ($CH_2ONO_2$); 5.80 ppm, d, J=17.8 Hz, 1.0 H (SCH); 6.80–9.00 ppm, m, 5.8 H (arom. H, NH, OH).

EXAMPLE XVII

N-acetyl-4-carboxy-2-[2-(2-nitroxyethoxy)phenyl]-thiazolidine

A solution of 0.9 ml of acetic anhydride in THF was added slowly at 0° C. to a solution of 2 g of the compound from Example XVI and 2.1 g of potassium carbonate in $H_2O$. The resulting solution was stirred for 1 hour, after which 1.0 g of potassium carbonate was added to the reaction mixture, followed by the addition of 1 ml of acetic anhydride. The reaction mixture was stirred for one and a half hours, after which a further 1.0 g of potassium carbonate and 1 ml of acetic anhydride were added. After finally stirring for a further 30 minutes, the solution was concentrated under vacuum and cooled in ice. The addition of dilute sulphuric acid gave a precipitate. This precipitate was filtered off, dried and recrystallised from methanol/ether. Yield 60%. Empirical formula $C_{14}H_{16}N_2O_7S$. Molecular weight 356. Melting point 159°–162° C. TLC system: ethyl acetate:methanol/1:1. $R_f$ 0.50.

NMR data (DMSO): 1.80 ppm, s, 2.0 H ($\frac{2}{3} \times CH_3$); 2.08 ppm, s, 1.0 H ($\frac{1}{3} \times CH_3$); 2.83–3.60 ppm, m, 2.0 H ($SCH_2$); 4.18–5.25 ppm, m, 5.0 H ($CH_2CH_2$, $CHCO_2$); 6.38 ppm, s, 1.0 H (CH); 6.80–8.20 ppm, 4.0 H (arom. H); 9.70 ppm, bs, 1.0 H (OH).

EXAMPLE XVIIIa 3-(2-Nitroxyethoxy)benzaldehyde 1.42 g of sodium were dissolved in 200 ml of ethanol. 7.5 g of 3-hydroxybenzaldehyde and 10.5 g of bromoethyl nitrate were added and the resulting solution was refluxed for 5 hours. The compound was purified by column chromatography (silica, $CH_2Cl_2$). Yield 19%. Melting point: oil.

$^1$H NMR ($CDCl_3$): 4.30 ppm, t, J=4.5 Hz, 2.0 H ($OCH_2$); 4.84 ppm, t, J=4.5 Hz, 2.0 H ($CH_2ONO_2$); 7.06–7.80 ppm, 4.0 H (arom. H); 9.93 ppm, s, 0.9 H (CH).

EXAMPLE XVIII

4-Carboxy-2-[3-(2-nitroxyethoxy)phenyl]thiazolidine

Prepared from the compound from Example XVIIIa as described in Example XVI. Yield 40%. Empirical formula $C_{12}H_{14}N_2O_6S$. Molecular weight 314. Melting point 117°–119° C. TLC system: methanol. $R_f$ 0.60.

NMR data (DMSO): 2.95–3.56 ppm, m, 2.0 H ($SCH_2$); 3.76–4.51 ppm, m, 3.0 H (phenoxy-$CH_2$, $CHCO_2$); 4.78–5.03 ppm, m, 2.0 H ($CH_2ONO_2$); 5.50 ppm, s, 0.3 H (0.3×CH); 5.69 ppm, s, 0.7 H (0.7×CH); 6.79–7.48 ppm, m, 4.0 H (arom. H).

EXAMPLE XIX

2-[3-(2-Nitroxyethoxy)phenyl]thiazolidine × HCl

A solution of 2 g of cysteamine × HCl and 2.6 g of potassium carbonate in water was added to a solution of 4 g of the compound from Example XVIIIa in methanol. The resulting solution was stirred for 10 minutes, concentrated in vacuo and then extracted with diethyl ether. After drying over magnesium sulphate, hydrochloric acid was added and the mixture was evaporated. The residue was treated with ethyl acetate, whereupon it solidified. Yield 25%. Empirical formula $C_{11}H_{15}ClN_2O_4S$. Molecular weight 306.5. Melting point 94°–98° C.

NMR data (DMSO): 2.88–4.00 ppm, m, 5.1 H (2×$CH_2$, $H_2O$); 4.28–4.45 ppm, m, 2.0 H (phenoxy-$CH_2$); 4.81–5.06 ppm, m, 2.0 H ($CH_2ON$); 5.77 ppm, s, 1.0 H (CH); 7.00–7.64 ppm, m, 4.0 H (arom. H); 8.40 ppm, bs, 1.0 H (NH); 10.80 ppm, bs, 1.1 H (HCl).

EXAMPLE XXa 3,5-Dinitro-2-(2-nitroxyethoxy)benzaldehyde 10 g of 2-(2-hydroxyethoxy)benzaldehyde were added at a temperature between −5° C. to +5° C. to nitric acid. After everything had been added, the reaction mixture was poured into water. The aqueous phase was extracted with ethyl acetate and the ethyl acetate layer was washed with aqueous sodium carbonate, dried over magnesium sulphate and evaporated. It was possible to isolate the title compound from the residue by chromatography (silica, ethyl acetate:petroleum ether 60–80/1:2).

Melting point 78°–80° C.

$^1$H NMR ($CDCl_3$): 4.47–4.70 ppm, m, 2.0 H (phenoxy-$CH_2$); 4.84–5.07 ppm, m, 2.0 H ($CH_2ON$); 8.89–9.10 ppm, m, 2.0 (arom. H); 10.44 ppm, s, 1.0 H (CHO).

EXAMPLE XX

4-Carboxy-2-[3,5-dinitro-2-(2-nitroxyethoxy)phenyl]-thiazolidine

Prepared from the compound from Example XXa and cysteine as described in example XVI. After concentration of the reaction medium, the precipitate was washed with water, dried in vacuo, washed thoroughly with diethyl ether and dried again. Yield 60%. Empirical formula $C_{12}H_{12}N_4O_{10}S$. Molecular weight 404. Melting point 135°–137° C. (decomposition). TLC system: ethyl acetate:acetic acid/20:1. $R_f$ 0.62.

NMR data (DMSO): 2.90–3.54 ppm, 2.0 H ($SCH_2$); 3.94–4.30 ppm, 1.0 H ($CHCO_2$); 4.37–4.63 ppm, m, 1.9 H (phenoxy-$CH_2$); 4.82–5.09 ppm, m, 2.0 H ($CH_2ON$); 5.77–6.15 ppm, m, 1.0 H (SCH); 8.58–9.14 ppm, m, 2.0 H (arom. H).

EXAMPLE XXIa

5-Nitro-2-(2-nitroxyethoxy)benzaldehyde

Isolated from the reaction mixture of the compound from Example XXa by chromatography.

$^1$H NMR ($CDCl_3$): 4.53 ppm, t, J=4.5 Hz, 2.0 H (phenyl-$OCH_2$); 4.94 ppm, t, J=4.5 Hz, 2.0 H ($CH_2O$-

NO$_2$); 7.12 ppm, d, J=9.4 Hz, 1.0 H (arom. H); 8.42 ppm, double doublet, J1=9.4 Hz, J2=3.1 Hz, 1.0 H (arom. H); 9.65 ppm, d, J=3.1 Hz, 0.9 H (arom. H); 10.44 ppm, s, 0.9 H (CH).

EXAMPLE XXI

4-Carboxy-2-[5-nitro-2-(2-nitroxyethoxy)phenyl]-thiazolidine

Prepared from the compound from Example XIIa as described in Example XVI. Empirical formula $C_{12}H_{13}N_3O_8S$. Molecular weight 359. Melting point 99°–101° C. TLC system:ethyl acetate:acetic acid/1:1. $R_f$ 0.64.

NMR ndata: 2.78–3.37 ppm, m, 1.9 H (SCH$_2$); 3.88–4.22 ppm, m, 1.0 H (CHCO); 4.41–4.68 ppm, m, 2.0 H (phenoxy-CH$_2$); 4.88–5.14 ppm, m, 2.0 H (CH$_2$ON); 5.68–5.94 ppm, m, 1.0 H (CHS); 7.30 ppm, d, J=9.2 Hz, 1.0 H (arom. H); 8.08–8.59 ppm, m, 2.0 H (arom. H).

EXAMPLE XXIIa

N-acetyl-4-carboxy-2-(2-phenylethyl)thiazolidine

A solution of 10 g of 3-phenylpropionaldehyde in THF was added to a solution of 10 g of cysteine in water. The resulting solution was stirred for 1 hour and then concentrated in vacuo. The precipitate was filtered off and washed with water and diethyl ether. The solid substance was dissolved in water which contained 12.5 g of potassium carbonate. 7.8 g of acetic anhydride were added at 0° C. and the resulting was stirred for 1 hour, after which the mixture was acidified to pH=2 with dilute sulphuric acid. This mixture was stirred for 30 minutes. The precipitate was filtered off, washed with water and dried. Yield 90%.

$^1$H NMR (DMOS): 1.54–2.86 ppm, m, 9.1 H (CH$_3$, CH$_2$S, CH$_2$, DMSO-d5); 3.10–3.66 ppm, m, 2.0 H (phenyl-CH$_2$); 4.56–5.44 ppm, m, 2.0 H (2×CH); 7.03–7.48 ppm, m, 6.0 H (arom. H, OH).

EXAMPLE XXII

N-acetyl-2-(2-phenylethyl)-4-[(4-nitroxymethylcyclohexyl)methoxycarbonyl]thiazolidine A solution of 4.2 g of dicyclohexylcarbodiimide in dichloromethane was added at 0° C. to a solution of 5.6 g of the compound from Example XXIIa, 1.9 g of 1,4-(trans)-cyclohexyldimethanol mononitrate ester and 2.6 g of 1-hydroxybenztriazole. The resulting solution was left to stand overnight and then filtered. The filtrate was washed successively with dilute hydrochloric acid and aqueous sodium carbonate, dried over magnesium sulphate and evaporated. The compound was purified by chromatography (silica, ethyl acetate:petroleum ether 40–60/2:3). Yield 70%. Empirical formula $C_{22}H_{30}N_2O_6S$. Molecular weight 422. Melting point: oil. TLC system: ethyl acetate:petroleum ether 40–60/1:1. $R_f$ 0.55.

NMR data: 0.86–2.40 ppm, m, 15.6 H (cyclohexyl-H, CH$_3$, CH$_2$); 2.58–2.98 ppm, m, 2.0 H (CH$_2$); 3.23–3.51 ppm, m, 2.0 H (CH$_2$); 3.93–4.13 ppm, m, 2.0 H (CH$_2$); 4.29 ppm, d, J=5.9 Hz, 2.0 H (CH$_2$ON); 4.71–5.62 ppm, m, 2.0 H (2×CH); 7.14–7.42 ppm, m, 5.0 H (arom. H).

EXAMPLE XXIIa

3-Bromo-4-(2-hydroxyethoxy)-5-methoxybenzaldehyde

Prepared from 10 g of 3-bromo-4-hydroxy-5-methoxybenzaldehyde as described in Example XIIa. Purified by chromatography (silica, ethyl acetate). Yield 50%.

$^1$H NMR (CDCl$_3$): 3.09–4.45 ppm, m, 8.0 H (CH$_3$, 2×CH$_2$, OH); 7.41 ppm, d, J=1.7 Hz, 1.0 H (arom. H); 7.67 ppm, d, J=1.7 Hz, 1.0 H (arom. H); 9.85 ppm, s, 1.0 H (CHO).

EXAMPLE XXIIIb

3-Bromo-5-methoxy-4-(2-nitroxyethoxy)benzaldehyde

Prepared from the compund from example XXIIIa as described in example XIIb. Yield 80%.

$^1$H NMR (CDCl$_3$): 3.92 ppm, s, 3.0 H (CH$_3$); 4.31–4.52 ppm, m, 2.0 H (phenoxy-CH$_2$); 4.73–4.98 ppm, m, 2.0 H (CH$_2$ON); 7.38 ppm, d, J=1.8 Hz, 1.0 H (arom. H); 7.66 ppm, d, J=1.8 Hz, 1.0 H (arom. H); 9.84 ppm, s, 0.9 H (CHO).

EXAMPLE XXIII

2-[3-Bromo-5-methoxy-4-(2-nitroxyethoxy)phenyl]-4-carboxythiazolidine

Prepared as described in example XVI. Yield 60%. Empirical formula $C_{13}H_{15}BrN_2O_7S$. Molecular weight 423. Melting point 129°–133° C. (decomposition). TLC system:ethyl acetate:acetic acid/9:1. $R_f$ 0.29.

NMR data (DMSO): 3.00–3.55 ppm, m, 2.0 H (SCH$_2$); 3.66–4.30 ppm, m, 7.0 H (CH$_3$, CHCO, phenoxy-CH$_2$); 4.72–4.92 ppm, m, 2.0 H (CH$_2$ON); 5.40–5.72 ppm, m, 1.0 H (SCH); 7.04–7.41 ppm, m, 2.0 H (arom. H).

EXAMPLE XXIVa

4-Formylphenoxyacetic acid

Prepared from 4-hydroxybenzaldehyde as described in Example Xa. Yield 40%. Melting point 195°–202° C.

$^1$H NMR (CDCl$_3$-DMSO): 4.66 ppm, s, 2.0 H (OCH$_2$); 7.00 ppm, d, J=9.0 Hz, 2.0 H (arom. H); 7.80 ppm, d, J=9.0 Hz, 2.0 H (arom. H); 9.84 ppm, s, 1.0 H (CH); 12.00 ppm, bs, 1.0 H (OH).

EXAMPLE XXIVb 2-(4-Formylphenoxy)-N-(2-nitroxyethyl)acetamide

Prepared from the compound from Example XXIVa as described in Example IXa. Yield 65%. Melting point 84°–87° C.

EXAMPLE XXIV

4-Carboxy-2-{4-[(2-nitroxyethyl)aminocarbonylmethoxy]phenyl}thiazolidine

Prepared from the compound from Example XXIVb as described in Example XVI. Yield 40%. Empirical formula $C_{14}H_{17}N_3O_7S$. Molecular weight 371. Melting point 120° C. (decomposition). TLC system: methanol. $R_f$ 0.71.

NMR data (DMSO): 3.00–3.68 ppm, m, 3.9 H (N-CH$_2$, SCH$_2$); 3.74–4.38 ppm, m, 1.0 H (CHCO); 4.42–4.74 ppm, m, 4.0 H (2×CH$_2$O); 5.46 ppm, s, 0.45 H (0.45×SCH); 5.61 ppm, s, 0.55 H (0.55×SCH); 6.79–7.10 ppm, m, 2.0 H (arom. H); 7.30–7.60 ppm, m, 2.0 H (arom. H); 8.37 ppm, bs, 0.9 H (CONH).

EXAMPLE XXVa

3-Chloro-6-(2-hydroxyethoxy)benzaldehyde

Synthesized from 25 g of 3-chloro-6-hydroxybenzaldehyde, 14 g of ethylene carbonate and 45 g of tetraethylammonium bromide as described in Example XIIa.

The compound was purified by chromatography (silica, ethyl acetate:petroleum ether 60-80/2:1). Yield 60%. Melting point 65°-68° C.

H NMR (CDCl$_3$): 2.87 ppm, bs, 0.8 H (OH); 3.90-4.32 ppm, m, 4.0 H (CH$_2$CH$_2$); 6.84-7.84 ppm, m, 3.0 H (arom. H); 10.34 ppm, s, 1.0 H (CH).

EXAMPLE XXVb

3-Chloro-6-(2-nitroxyethoxy)benzaldehyde

Prepared from 8 g of the compound from Example XXVa, 25 ml of nitric acid and 12.5 ml of acetic anhydride as described in Example XIIb. The compound was purified by chromatography (silica, CH$_2$Cl$_2$). Yield 60%.

H NMR (CDCl$_3$): 4.34 ppm, t, J=4.5 Hz, 1.9 H (phenyl-OCH$_2$); 4.90 ppm, t, J=4.5 Hz, 1.9 H (CH$_2$ONO$_2$); 6.80-7.87 ppm, m, 3.0 H (arom. H); 10.34 ppm, s, 0.9 H (CH).

EXAMPLE XXV

4-Carboxy-2-[5-chloro-2-(2-nitroxyethoxy)phenyl]-thiazolidine

Prepared from 4.0 g of the compound from Example XXVb and 5 g of cysteine as described in Example XVI. Yield 75%. Empirical formula C$_{12}$H$_{13}$ClN$_2$O$_6$S. Molecular weight 348.5. Melting point 134°-135° C. TLC system:methanol. R$_f$0.73.

NMR data (DMSO): 2.80-3.49 ppm, m, 2.0 H (SCH$_2$); 3.71-4.18 ppm, m, 1.0 H (CHCO); 4.25-4.50 ppm, 2.0 H (phenoxy-CH$_2$); 4.72-5.03 ppm, m, 2.0 H (CH$_2$ON); 5.64 ppm, s, 0.75 H (0.75×CH); 5.83 ppm, s, 0.25 H (0.25×CH); 6.84-7.73 ppm, m, 3.1 H (aromo. H).

EXAMPLE XXVI

4-Carboxy-5,5-dimethyl-2-[(2-nitroxyethoxy)phenyl]-thiazolidine

A solution of 2.0 g of D-penicillamine in water was added to a solution of 2.0 g of the compound from Example XVIb in tetrahydrofuran. The resulting solution was concentrated under reduced pressure until a precipitate resulted. The solvent was decanted off and the precipitate taken up in ethyl acetate. The organic layer was dried over sodium sulphate and filtered. The addition of petroleum ether 60-80 to the filtrate allowed the title compound to crystallise. Yield 60%. Empirical formula C$_{14}$H$_{18}$N$_2$O$_6$S. Molecular weight 342. Melting point 98°-101° C. TLC system: ethanol:ethyl acetate/1:1. R$_f$0.66.

NMR data (CDCl$_3$): 1.16-1.82 ppm, m, 6.0 H (2×CH$_3$); 3.70-4.05 ppm, m, 1.0 H (CHCO$_2$); 4.20-4.53 ppm, m, 2.0 H (phenyl-OCH$_2$); 4.75-5.12 ppm, m, 2.0 H (CH$_2$ONO$_2$); 5.90-6.10 ppm, m, 1.0 H (SCH); 6.73-7.72 ppm, m, 4.0 H (arom. H); 9.06 ppm, bs, 2.0 H (NH, CO$_2$H).

EXAMPLE XXVII

2-[(2-Nitroxyethoxy)phenyl]thiazolidine oxalate hydrate

A solution of 5.0 g of the compound from Example XVIb in ethanol was added to a solution of 2.4 g of cysteamine×HCl and 3 g of potassium carbonate in water. The resulting solution was concentrated under reduced pressure and extracted with diethyl ether. The ether phase was dried over sodium sulphate and filtered. A saturated solution of oxalic acid in diethyl ether was added and the precipitate was filtered off and recystallised from methanol/diethyl ether. Yield 40% Empirical formula C$_{13}$H$_{16}$N$_2$O$_8$S. Molecular weight 360. Melting point 118°-120° C. TLC system: diethyl ether. R$_f$ 0.71.

NMR data (DMSO): 3.33-4.06 ppm, m, 4.0 H (SCH$_2$CH$_2$); 4.74-4.98 ppm, m, 2.0 H (phenyl-OCH$_2$); 5.32-5.56 ppm, m, 2.0 H (CH$_2$ONO$_2$); 6.22 ppm, s, 1.0 H (SCH); 7.17-8.14 ppm, m, 9.0 H (arom. H, NH, H$_2$O, 2×CO$_2$H).

EXAMPLE XXVIII

4-Ethoxycarbonyl-2-[2-(2-nitroxyethoxy)phenyl]-thiazolidine 4-toluenesulphonate

A solution of 6 g of the compound from Example XVIb in tetrahydrofuran was added to a solution of 4.0 g of L-cysteine ethyl ester.HCl and 3.0 g of potassium carbonate in water. The resulting mixture was concentrated under reduced pressure and extracted with diethyl ether. After drying over sodium sulphate, a solution of 4-toluenesulphonic acid in ether was added and the precipitate was filtered off and recrystallised from tetrahydrofuran/petroleum ether 60-80. Yield 40% Empirical formula C$_{21}$H$_{26}$N$_2$O$_9$S. Molecular weight 514. Melting point 137°-140° C. TLC system: dichloromethane. R$_f$0.42.

NMR data (CDCl$_3$): 1.24 ppm, t, J=7.2 Hz, 3.0 H (ester-CH$_3$); 2.34 ppm, s, 3.0 H (phenyl-CH$_3$); 3.22-3.96 ppm, m, 2.0 H (SCH$_2$); 4.03-4.37 ppm, m, 4.0 H (ester-CH$_2$, phenyl-OCH$_2$); 4.76-5.19 ppm, m, 3.0 H (CHCO$_2$, CH$_2$ONO$_2$); 6.27 ppm, d, J=10.8 Hz, 1.0 H (SCH); 6.64-7.80 ppm, m, 8.0 H (arom. H); 8.90 ppm, bs, 1.0 H.

EXAMPLE XXIXa

4-Bromomethyl-(trans)-cyclohexylmethanol

A solution of 60 g of 1,4-(trans)-cyclohexyldimethanol in 300 ml of 48% hydrobromic acid was heated at 90° C. for 20 hours, while this solution was extracted continuously with petroleum ether 100-140. After cooling the reaction mixture, the petroleum ether 100-140 was evaporated off and the residue was purified by distillation under reduced pressure. Yield 50%. Boiling point 150° C. (10 mm Hg).

$^1$H NMR (CDCl$_3$): 0.72-2.26 ppm, m, 10.0 H (cyclohexyl-H); 3.25-3.58 ppm, m, 5.0 H (BrCH$_2$, CH$_2$OH).

EXAMPLE XXIXb

2-[(4-Hydroxymethyl-(trans)-cyclohexyl)methoxy]benzaldehyde

A mixture of 13 g of salicyaldehyde, 20 g of the compound from Example XXIXa and 5.8 g of potassium hydroxide in 100 ml of dimethyl sulphoxide was heated at 130° C. for 4 hours, with stirring. After cooling to room temperature, the mixture was diluted with water and the resulting mixture was extracted with diethyl ether. After evaporation of the ether, the residue was purified by chromatography (silica, ethyl acetate: petroleum ether 60-80/1:2). Yield 38%.

$^1$H NMR (CDCl$_3$): 0.85-2.11 ppm, m, 11.0 H (cyclohexyl-H, OH); 3.50 ppm, d, J=5.6 Hz, 2.0 H (hydroxy-CH$_2$); 3.92 ppm, d, J=5.6 Hz, 2.0 H (phenoxy-CH$_2$); 6.87-7.92 ppm, m, 4.0 H (arom. H); 10.53 ppm, s, 1.0 H.

EXAMPLE XXIXc

2-{[4-Nitroxymethyl-(trans)-cyclohexyl]methoxy}benzaldehyde

A mixture of 11.1 ml of acetic anhydride and 4.6 ml of nitric acid was added at 0° C. to a solution of 8.0 g of the compound from Example XXIXb in ethyl acetate. After everything had been added, the mixture was stirred for a further 15 minutes and then poured into water. This mixture was stirred for 1 hour and then extracted with ethyl acetate. After drying and evaporating off the ethyl acetate, the residue was purified by chromatography (silica, ethyl acetate: petroleum ether 60–80/1:4). Yield 76%.

$^1$H NMR (CDCl$_3$): 0.80–2.17 ppm, m, 10.0 H (cyclohexyl-H); 3.88 ppm, d, J=5.4 Hz, 2.0 H (phenoxy-CH$_2$); 3.92 ppm, d, J=5.8 Hz, 2.0 H (CH$_2$ONO$_2$); 6.87–7.95 ppm, m, 4.0 H (arom. H); 10.53 ppm, s, 1.0 H (CH).

EXAMPLE XXIX

4-Carboxy-2-(2-{[4-nitroxymethyl-(trans)-cyclohexyl]methoxy}phenyl)thiazolidine

Synthesized from 3.0 g of the compound from Example XXIXc and 3.0 g of cysteine as described in Example XVI. Yield 60%. Empirical formula C$_{18}$H$_{24}$N$_2$O$_6$S. Molecular weight 396. Melting point 108°–111° C. TLC system: dichloromethane: petroleum ether 60–80/1:1. R$_f$ 0.57.

NMR data (DMSO): 0.67–2.21 ppm, m, 10.0 H (cyclohexyl-H); 2.73–4.58 ppm, m, 7.0 H (CHCO$_2$, SCH$_2$, 2×OCH$_2$); 5.63 ppm, s, 0.4 H (0.4×SCH); 5.93 ppm, s, 0.6 H (0.6×SCH); 3.72–7.81 ppm, m, 6.0 H (arom.H, CO$_2$H,NH).

EXAMPLE XXXa 2-(2,2-Dimethyl-3-hydroxypropoxy)benzaldehyde

A solution of 20 g of salicyaldehyde, 30 g of 3-bromo-2,2-dimethylpropanol and 22 g of potassium carbonate in DMF was refluxed for 24 hours. After evaporation, the residue was dissolved in ethyl acetate and washed with water. The organic phase was dried over magnesium sulphate and evaporated. The residue was purified by chromatography (silica, dichloromethane). Yield 25%.

$^1$H NMR (CDCl$_3$): 1.06 ppm, s, 6.0 H (2×CH$_3$); 2.60 ppm, bs, 1.0 H (OH); 3.60 ppm, s, 2.0 H (hydroxyl-CH$_2$); 3.90 ppm, s, 2.0 H (phenoxy-CH$_2$); 6.90–7.90 ppm, m, 4.0 H (arom. H); 10.40 ppm, s, 1.0 H (CHO).

EXAMPLE XXXb 2-(2,2-Dimethyl-3-nitroxypropoxy)benzaldehyde

Prepared from the compound from Example XXXa as described in example XIIb. Purified by chromatography (silica, dichloromethane). Yield 82%.

$^1$H NMR (CDCl$_3$): 1.20 ppm, s, 6.0 H (2×CH$_3$); 3.90 ppm, s, 2.0 H (phenoxy-CH$_2$); 4.46 ppm, s, 2.0 H (CH$_2$ON); 6.88–7.98 ppm, m, 4.0 H (arom. H); 10.50 ppm, s, 1.0 H (CHO).

EXAMPLE XXX

4-Carboxy-2-[2-(2,2-dimethyl-3-nitroxypropoxy)-phenyl]thiazolidine

A solution of 3.0 g of the compound from Example XXXb in tetrahydrofuran was added to a solution of 3.0 g of cysteine in water. Additional tetrahydrofuran was added until a clear solution resulted. This solution was concentrated under reduced pressure. The precipitate, which formed during concentration of the reaction mixture, was filtered off and crystallised from methanol. Yield 83%. Empirical formula C$_{15}$H$_{20}$N$_2$O$_6$S. Molecular weight 356. Melting point 105°–108° C. TLC system: tetrahydrofuran: ethyl acetate/1:1. R$_f$ 0.58.

NMR data (DMSO): 1.06 ppm, s, 6.0 H (2×CH$_3$); 2.77–4.29 ppm, m, 6.0 H (phenoxy-CH$_2$, CHCO$_2$, SCH$_2$, NH); 4.60 ppm, s, 2.0 H (CH$_2$ONO$_2$); 5.71 ppm, s, 0.4 H (0.4×SCH); 5.99 ppm, s, 0.6 H (0.6×SCH); 6.86–7.96 ppm, m, 5.0 H (arom. H, CO$_2$H).

EXAMPLE XXXI

4-Carboxy-N-(2,2-dimethyl-3-nitroxypropionyl)-2-phenylthiazolidine

A solution of 5.2 g of 2,2-dimethyl-3-nitroxypropanoyl chloride in 100 ml of tetrahydrofuran was added at 0° C. under nitrogen to a solution of 6.0 g of 4-carboxy-2-phenylthiazolidine and 4.0 g of potassium carbonate in a mixture of 50 ml of tetrahydrofuran and 150 ml of water. After stirring the resulting solution for 45 minutes the mixture was concentrated under reduced pressure to about 150 ml and then acidified to pH=2 with citric acid. The resulting mixture was extracted with diethyl ether and the organic phase was dried over sodium sulphate and evaporated. The residue was purified by chromatography (silica, petroleum ether 60–80: ethyl acetate: acetic acid/8:8:1). Yield 38%. Empirical formula C$_{15}$H$_{18}$N$_2$O$_6$S. Molecular weight 354. Melting point 35°–38° C. TLC system: petroleum ether 60–80: ethyl acetate: acetic acid/4:4:1. R$_f$ 0.50.

NMR data (CDCl$_3$): 1.24 ppm, s, 6.0 H (2×CH$_3$); 2.53–3.21 ppm, m, 2.0 H (SCH$_2$); 4.33–5.23 ppm, m, 4.0 H (CH$_2$ONO$_2$, CHNCH); 6.58–7.50 ppm, m, 6.0 H (arom. H, CO$_2$H).

EXAMPLE XXXIIa 2-(3-Hydroxypropoxy)benzaldehyde

Synthesized from salicylaldehyde and 3-chloropropanol as described in Example XXIXb.

EXAMPLE XXXIIb 2-(3-Nitroxypropoxy)benzyldehyde

Prepared from the compound of Example XXXIIa as described in Example XXXIXc.

EXAMPLE XXXII

4-Carboxy-2-[2-(3-nitroxypropoxy)phenyl]thiazolidine

Prepared from the compound of Example XXXIIb and cysteine as described in Example XVI. Yield 30%. Empirical formula: C$_{13}$H$_{16}$N$_2$O$_6$S. Molecular Weight: 328. Melting Point: 131°–134° C. TLC System: methanol:ethyl acetate/1:1. R$_f$: 0.64.

NMR data (DMSO): 1.91–2.30 ppm, m, 2.0 H (C—CH$_2$—C), 2.82–3.46 ppm, m, 2.0 H (SCH$_2$), 3.69–4.24 ppm, m, 3.0 H (phenyl-OCH$_2$, SCCH); 4.55–4.85 ppm, m, 2.0 H (CH$_2$ONO$_2$); 5.63 ppm, s, 0.4 H (0.4×CH), 5.86 ppm, s, 0.6 H (0.6×CH); 6.70–7.51 ppm, m, 4.0 H (arom. H); 8.00 ppm, bs, 1.8 H (COH, NH).

EXAMPLE XXXIII

4-Carboxyl-N-(2,2-dimethyl-3-nitroxypropionyl)-2-phenylthiazolidine

A solution of 5.2 g of 2.2-dimethyl-3-nitroxypropanoylchloride (J. Hutter, Schwarz Pharma AG, EP 0362575) in 100 ml of tetrahydrofurane was added to a solution of 6.0 g of 4-carboxy-2-phenylthiazolidine and 4.0 g of potassium carbonate in a mixture of 50 ml of tetrahydrofurane and 150 ml of water at 0° C., under nitrogen. After stirring the resulting solution for 45 minutes, the mixture was concentrated under reduced pressure to approximately 150 ml and subsequently acidified to pH=2 with citric acid. The resulting mixture was extracted with diethyl ether, the organic phase dried over sodium sulfate and evaporated. The residue was purified by chromatographie (silica, pe60–80:ethyl acetate:acetic acid/8:8:1. Yield: 38%. Empirical formula: $C_{15}H_{18}N_2O_6S$. Molecular Weight: 354. TLC system: pe60–80:ethyl acetate:acetic acid/4:4:1. $R_f$: 0.50.

NMR data ($CDCl_3$): 1.24 ppm, s, 6.0 H ($2 \times CH_3$); 2.53–3.21 ppm, m, 2.0 H ($SCH_2$); 4.33–5.23 ppm, m, 4.0 H ($CH_2ONO_2$, CHNCH); 6.58–7.50 ppm, m, 6.0 H (arom. H, $CO_2H$).

EXAMPLE XXXIV

4-Carboxy-2-[2-(4-nitroxybutoxy)phenyl]thiazolidine

Prepared as described for Example XVI. Yield: 30%. Empirical formula: $C_{14}H_{18}N_2O_6S$. Molecular weight: 432. Melting point: 108°–110° C. TLC system: methanol:ethyl acetate/1:1. $R_f$: 0.74.

NMR data (DMS): 1.57–2.09 ppm, m, 4.0 H ($CCH_2CH_2C$); 2.75–4.47 ppm, m, 2.0 H ($SCH_2$); 3.68–4.22 ppm, m, 4.0 H (SCCH, NH, phenoxy-$CH_2$); 4.42–4.70 ppm, m, 2.0 H ($CH_2ONO_2$); 5.64 ppm, s, 0.3 H ($0.3 \times CH$); 5.86 ppm, s, 0.7 H (0.733 CH); 6.77–7.54 ppm, m, 4.9 H (arom. H, $CC_2H$).

EXAMPLE XXXVa

3-Nitro-4-(2-nitroxyethoxy)benzaldehyde

Isolated from the reaction mixture described in Example XIIIb by chromatography.

EXAMPLE XXXV

4-Carboxy-2-[3-4-(2-nitroxyethoxy)phenyl]thiazolidine

Prepared from the compound from Example XXXVa as described in Example XVI. Yield: 33%. Empirical formula: $C_{12}H_{13}N_3O_8S$. Molecular weight: 359. Melting point: 149°–150° C.

NMR data (DMSO-$d_6$): 2.87–427 ppm, m, 5.0 H ($CO_2H$, NH, $CH_2CH$(, 4.41–4.62 ppm, m, 2.0 H (phenoxy-$CH_2$); 4.78–5.02 ppm, m, 1.0 H ($CH_2ONO_2$); 5.55 ppm, s, 0.6 H ($0.6 \times CH$), 5.73 ppm, s, 0–4 H ($0.4 \times CH$); 7.22–8.22 ppm, m, 3.0 H (arom. H).

EXAMPLE XXXVI

4-Carboxy-2-[2-(2-nitroxypropoxy)phenyl]thiazolidine

Prepared from 2-(2-nitroxypropoxy)benzaldehyde and cysteine as described in Example XVI. Yield: 30%. Empirical formula: $C_{13}H_{16}N_2O_6S$. Molecular weight: 328. Melting point: 127°–130° C.

NMR data (DMSO-$D_6$): 1.27–1.63 ppm, m, 3.0 H ($CH_3$); 2.75–3.50 ppm, m, 2.0 H ($SCH_2$); 3.71–4.41 ppm, m, 1.0 H (phenoxy-$CH_2$, $CHCO_2$, $CHCO_2$); 5.37–5.74 ppm, m, 1.4 H ($0.4 \times SCH$, $CHONO_2$); 5.91 ppm, s, 0.6 H ($0.6 \times SCH$); 6.86–7.67 ppm, m, 4.0 H (arom. H).

Pharmacology

The pharmacological activity of the compounds according to the invention was demonstrated in vivo in anesthetized rabbits and in vitro in the so-called rat aorta assay.

In the anesthetized rabbits, the decrease of arterial blood pressure and the effect on the heart rate after infusion of the test compounds was determined. Surprisingly, the compounds according to the invention have only a small influence on the heart rate, whereas they produce a marked decrease of the arterial blood pressure.

In the rat aorta assay, the compounds according to the invention are—in contrast to e.g. nifedipine—able to effect an up to 100% relaxation of a contraction of the rat aorta induced by phenylephrine.

In the tables following the detailed description of the in vivo and in vitro experiments, the compounds investigated are identified by numbers which correspond to the numbers in the Examples.

Anesthetized rabbit experiments

Animals anesthesia and surgical procedures

New Zealand white rabbits (2.5–3 kg) were anesthetized (30 mg$\times$kg$^{-1}$ pentobarbitone, i.v., supplemental doses as needed). Tracheotomy was performed, and an intra-tracheal cannula was inserted. No artificial ventilation was applied and body temperature was maintained at 37°–38° C.

Left ventricular pressure (LVP) was measured (Millar Mikro-Tip catheter via the right carotid artery with transducer in the left ventricle). The LVP signal was differentiated electronically to obtain the rate of change of LVP (LV dP/dt). The heart rate (HR) was derived from the LVP pulse signal. The jugular vein was cannulated for infusion of the test compounds. Aortic blood pressure (SAP and DAP) was monitored (Gould-Statham pressure transducer) by inserting a polyethylene catheter filled with heparin (50 IU$\times$ml$^{-1}$) through the femoral artery into the abdominal aorta. Heparin (150 IU$\times$kg$^{-1}$, i.v.) was administered to prevent blood clotting.

After completion of surgical procedures, the rabbits were allowed to recover for 15 minutes before drug administration was started.

Infusion of test compounds and test protocol

Drugs were infused at constant rate (0.5 ml$\times$min$^{-1}$) for 10 minutes at various doses, resulting in a typical dose range of 2.0, 20.0 and 200 $\mu$g$\times$kg$^{-1}\times$min$^{-1}$ (2.5 kg rabbit).

Due to poor solubility, 1 mg$\times$ml$^{-1}$ solutions of all the compounds tested were prepared in Intralipid ® 10%, containing 10% (v/v) dimethyl sulfoxide (DMSO). Infusion of this solvent at 0.5 ml$\times$min$^{-1}$ in the anesthetized rabbit, as was performed at the aforementioned highest dose, did not lead to changes in hemodynamic state. At the infusion of lower doses, the 1 mg$\times$ml$^{-1}$ stock solutions were diluted with Intralipid ® 10%.

Definition of effects

The presented data are based on the effects obtained at the end of the 10 min infusion period at the highest dose tested (150–200 $\mu$g$\times$kg$^{-1}\times$min$^{-1}$). The indicated ratings are referring to the effects (decrease, defined as percentage of basal value before infusion of the drug) on arterial blood pressure as follows:

| | |
|---|---|
| No decrease or decrease less than 5% | Inactive |
| Decrease between 5 and 40% | Active |
| Decrease greater than 40% | Very Active |

TABLE 1

Effects of the compounds according to the invention on the arterial blood pressure in the anesthetized rabbit.

| Example No. | Activity with regard to the lowering of blood pressure |
|---|---|
| III | Active |
| XIII | Active |
| XV | Active |
| XVI | Active |
| XX | Active |
| XXI | Active |
| XXII | Active |
| XXV | Active |
| XXVI | Active |
| XXVII | Active |
| XXVIII | Active |
| XXIX | Active |
| XXX | Active |
| XXXVI | Active |

*Active: Decrease in blood pressure between 5 and 40%.

In vitro rat aorta assay

Strips of thoracial rat aortae (without aortic arch, helically cut; length 1–1.5 cm; width about 2 mm) were place in an organ bath [20 ml; Krebs Ringer medium bubbled with $O_2/CO_2$ (95/5%) at 37° C.]. A resting tension of 0.5 g was applied and the preparations were equilibrated during 100 min (fresh buffer solution every 20 min). The strips were isotonically contracted with $10^{-7}M$ phenylephrine.

Drug-induced relaxation was tested at increasing concentration (half log steps), till maximal or full relaxation (corresponding to basal precontraction value of organ length) had been reached.

Responses were calculated as change in organ length relatively to maximal displacement by contraction, $EC_{50}$ values corresponding to the drug concentration at which residual contraction is 50% of maximum.

TABLE 2

Effects of the compounds according to the invention on the contracted rat aorta.

| Example No. | $EC_{50}$ (mean, μM) | S.D. | Range | N |
|---|---|---|---|---|
| I | 0.7500 | 0.3700 | 0.4–1.5 | 6 |
| II | 0.7400 | 0.5000 | 0.1–2 | 18 |
| III | 0.0980 | 0.3300 | 0.06–0.15 | 4 |
| IV | 9.5000 | 6.6900 | 2–20 | 4 |
| V | 0.3300 | 1.2700 | 0.04–0.7 | 5 |
| VI | 1.6200 | 1.2600 | 0.2–4 | 6 |
| VII | 0.0200 | 0.0000 | 0.02–0.02 | 3 |
| VIII | 1.8800 | 1.3300 | 0.6–4 | 4 |
| IX | 0.7000 | 0.6600 | 0.1–2 | 6 |
| X | 0.3900 | 0.2400 | 0.03–0.8 | 6 |
| XI | 0.2700 | 0.1200 | 0.1–0.4 | 3 |
| XII | 0.6500 | 0.1400 | 0.5–0.9 | 6 |
| XIII | 0.02200 | 0.0037 | 0.02–0.03 | 6 |
| XIV | 0.2300 | 0.1700 | 0.1–0.6 | 6 |
| XV | 0.0070 | 0.0035 | 0.001–0.01 | 6 |
| XVII | 0.7200 | 0.9400 | 0.01–3 | 8 |
| XVIII | 0.0470 | 0.0390 | 0.002–0.1 | 6 |
| XIX | 0.0097 | 0.0005 | 0.009–0.01 | 6 |
| XX | 0.2200 | 0.1700 | 0.1–0.5 | 6 |
| XXI | 0.0250 | 0.0110 | 0.01–0.04 | 6 |
| XXII | 0.0230 | 0.0130 | 0.007–0.04 | 6 |
| XXIII | 0.8200 | 0.5900 | 0.1–2 | 6 |
| XXIV | 0.9000 | 0.5400 | 0.4–2 | 6 |

TABLE 2-continued

Effects of the compounds according to the invention on the contracted rat aorta.

| Example No. | $EC_{50}$ (mean, μM) | S.D. | Range | N |
|---|---|---|---|---|
| XXV | 0.0200 | 0.0100 | 0.008–0.04 | 6 |
| XXVI | 0.0570 | 0.0140 | 0.04–0.08 | 6 |
| XXVII | 0.0067 | 0.0024 | 0.005–0.01 | 6 |
| XXVIII | 0.0094 | 0.0057 | 0.006–0.02 | 9 |
| XXIX | 0.0210 | 0.0150 | 0.008–0.05 | 6 |
| XXX | 0.1020 | 0.0490 | 0.04–0.2 | 6 |
| XXXII | 0.0370 | 0.0200 | 0.01–0.007 | 6 |
| XXXIII | 2.7700 | 3.3700 | 0.003–10 | 7 |
| XXXIV | 0.0170 | 0.0300 | 0.007–0.1 | 9 |
| XXXV | 0.0540 | 0.0640 | 0.001–0.2 | 9 |
| XXXVI | 0.0480 | 0.0290 | 0.02–0.1 | 6 |

$EC_{50}$ = Concentration (μm) at which residual contraction is 50% of maximum;
S.D. = Standard deviation
N = Number of rat aortas tested

We claim:
1. A thiazolidine derivative having at least one organic nitrate ester group and of formula 1,

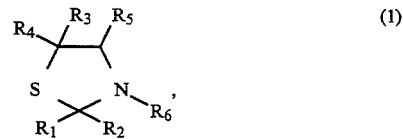

(1)

$R_1$ represents H or 1-4C-alkyl,
$R_2$ represents H, 1-6C-alkyl, 4-8C-cycloalkyl, phenyl-1-3C-alkyl or a group of formula 2,

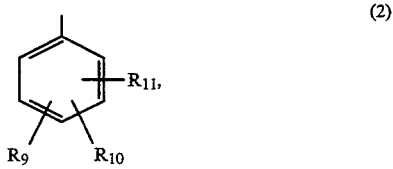

(2)

wherein
$R_9$, $R_{10}$, and $R_{11}$ simultaneously or separately represent H, 1-6C-alkyl, 1-6C-alkoxy, 4-8C-cycloalkyl, 4-8C-cycloalkoxy, F, Cl, Br, $NO_2$, nitroxy-2-6C-alkoxy, nitroxy-4-8C-cycloalkoxy, nitroxy-1-2C-alkyl-4-8C-cycloalkyl-1-2C-alkoxy or a group

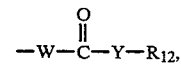

wherein
W represents a bond or —$OCH_2$—,
Y represents an oxygen atom or an imino group and $R_{12}$ represents H, 1-4C-alkyl, 4-8C—cycloalkyl, nitroxy-2-6C-alkyl or nitroxy-4-8C-cycloalkyl,
$R_3$ and $R_4$ represent H or 1-4C-alkyl,
$R_5$ represents H or

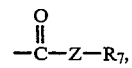

wherein
Z represents an oxygen atom or an imino group and $R_7$ represents H, 1-4C-alkyl, 4-8C-cycloalkyl, nitroxy-2-6C-alkyl, nitroxy-4-8C-cycloalkyl, nitroxy-1-2C-alkyl-4-8C-cycloalkyl-1-2C-alkyl or 4-nitroxy-2,6-dioxabicyclo[3.3.0]oct-8-yl, and $R_6$ represents H or —X—$R_8$,
wherein
X represents carbonyl or sulfonyl and
$R_8$ represents 1-4C-alkyl, 4-8C-cycloalkyl, nitroxy-2-6C-alkyl, nitroxy-4-8C-cycloalkyl, phenyl or 1-4C-alkylphenyl,
or a salt thereof.

2. A thiazolidine derivative of formula 1 according to claim 1, wherein
$R_1$ represents H,
$R_2$ represents H, 1-4C-alkyl, phenyl-1-2C-alkyl or a group of formula 2 according to claim 1,
wherein
$R_9$, $R_{10}$ and $R_{11}$ simultaneously or separately represent H, 1-6C-alkoxy, Cl, Br, $NO_2$, nitroxy-2-6C-alkoxy, nitroxy-1-2C-alkyl-4-8C-cycloalkyl-1-2C-alkoxy or a group

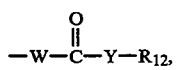

wherein
W represents a bond or a group —$OCH_2$—,
Y represents an oxygen atom or an imino group and
$R_{12}$ represents H or nitroxy-2-6C-alkyl,
$R_3$ and $R_4$ represent H or methyl,
$R_5$ represents H or a group

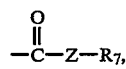

wherein
Z represents an oxygen atom or an imino group and
$R_7$ represents H, 1-4C-alkyl, nitroxy-2-4C-alkyl, nitroxymethyl-4-8C-cycloalkylmethyl or 4-nitroxy-2,6-dioxabicyclo[3.3.0]oct-8-yl, and
$R_6$ represents H or a group —X—$R_8$,
wherein
X represents carbonyl or sulfonyl and
$R_8$ represents 1-4C-alkyl, nitroxy-2-6C-alkyl, phenyl or 1-3C-alkylphenyl,
or a salt thereof.

3. A thiazolidine derivative of formula 1 according to claim 1, wherein
$R_1$ represents H,
$R_2$ represents phenylethyl or a group of formula 2 according to claim 1,
wherein
$R_9$, $R_{10}$ and $R_{11}$ simultaneously or separately represent H, methoxy or nitroethoxy,
$R_3$ and $R_4$ represent H,
$R_5$ represents H or a group

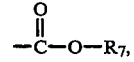

wherein
$R_7$ represents H or 4-nitromethylcyclohexylmethyl, and
$R_6$ represents H,
or a salt thereof.

4. A pharmaceutical composition comprising an effective amount of a thiazolidine derivative of claim 1 or of a pharmaceutically acceptable salt thereof and a suitable carrier.

* * * * *